(12) United States Patent
Lance et al.

(10) Patent No.: US 10,953,217 B2
(45) Date of Patent: Mar. 23, 2021

(54) CATHETER CONNECTION SYSTEM FOR ULTRAVIOLET LIGHT DISINFECTION

(71) Applicant: PuraCath Medical, Inc., San Francisco, CA (US)

(72) Inventors: Justin A. Lance, Hollister, CA (US); Stephen Bower, Morgan Hill, CA (US); John E. Ashley, Danville, CA (US); Jeffrey Etter, Hayward, CA (US); Julia A. Rasooly, San Francisco, CA (US); Michael Rasooly, San Francisco, CA (US); Benjamin S. Arnett, Morgan Hill, CA (US)

(73) Assignee: PuraCath Medical, Inc., San Francisco, CA (US)

( * ) Notice: Subject to any disclaimer, the term of this patent is extended or adjusted under 35 U.S.C. 154(b) by 532 days.

(21) Appl. No.: 15/074,854

(22) Filed: Mar. 18, 2016

(65) Prior Publication Data

US 2016/0271312 A1 Sep. 22, 2016

Related U.S. Application Data

(60) Provisional application No. 62/135,080, filed on Mar. 18, 2015, provisional application No. 62/238,644, filed on Oct. 7, 2015.

(51) Int. Cl.
*A61M 39/16* (2006.01)
*A61M 1/28* (2006.01)
(Continued)

(52) U.S. Cl.
CPC ........... *A61M 39/16* (2013.01); *A61L 2/0047* (2013.01); *A61M 1/285* (2013.01); *A61M 39/26* (2013.01); *A61M 2039/167* (2013.01)

(58) Field of Classification Search
CPC ............ A61M 39/16; A61M 2039/167; A61M 1/285; A61M 39/14; A61M 39/26;
(Continued)

(56) References Cited

U.S. PATENT DOCUMENTS 3,517,669 A 6/1970 Buono et al.
3,572,375 A 3/1971 Rosenberg
(Continued)

FOREIGN PATENT DOCUMENTS

CN 102536011 A 7/2012
CN 103536443 A 1/2014
(Continued)

OTHER PUBLICATIONS

Bak et al.; Disinfection of *Pseudomonas aeruginosa* biofilm contaminated tube lumens with ultraviolet C light emitting diodes; Biofouling: The Journal of Bioadhesion and Biofilm Research; 26(1); pp. 31-38; Jan. 2010.
(Continued)

*Primary Examiner* — Jenna Zhang
(74) *Attorney, Agent, or Firm* — Shami Messinger PLLC

(57) ABSTRACT

Systems and methods of disinfection of catheter connections are provided. A transfer catheter connector can include a UV-transparent window at its distal end and a sealing plunger proximal to the UV-transparent window. A solution set connector can be inserted inside a portion of the transfer catheter connector to connect a solution set and transfer catheter. The solution set connector comprises a lumen covered by a leading membrane surface; a sealing surface configured to sealingly engage the window surface, and a piercing member configured to pierce the membrane surface. The sealing plunger, membrane surface, and window define a disinfection zone. The connectors can be connected in a disinfection position configuration in which flow is not (Continued)

permitted between the catheters and the connectors are irradiated with UV light. After disinfection, the connectors are advanced to a flow position in which the piercing member pierces the membrane surface, enabling flow between the catheters.

15 Claims, 23 Drawing Sheets

(51) Int. Cl.
*A61L 2/00* (2006.01)
*A61M 39/26* (2006.01)

(58) Field of Classification Search
CPC .............. A61M 39/165; A61M 39/221; A61M 2039/1072; A61M 2039/1066; A61L 2/0047
See application file for complete search history.

(56) References Cited

U.S. PATENT DOCUMENTS

| | | | |
|---|---|---|---|
| 3,626,938 A | 12/1971 | Versaci | |
| 3,986,508 A * | 10/1976 | Barrington | A61L 2/00 604/411 |
| 4,146,055 A | 3/1979 | Ryder et al. | |
| 4,209,013 A | 6/1980 | Alexander et al. | |
| 4,232,428 A | 11/1980 | Johansson | |
| 4,242,310 A | 12/1980 | Greff et al. | |
| 4,256,135 A | 3/1981 | Hannah | |
| 4,336,223 A | 6/1982 | Hillman | |
| 4,340,052 A | 7/1982 | Dennehey et al. | |
| 4,346,704 A | 8/1982 | Kulle | |
| 4,412,834 A * | 11/1983 | Kulin | A61M 39/16 137/625.41 |
| 4,433,244 A | 2/1984 | Hogan | |
| 4,439,188 A | 3/1984 | Dennehey et al. | |
| 4,440,207 A | 4/1984 | Genatempo et al. | |
| 4,457,749 A * | 7/1984 | Bellotti | A61M 39/221 604/244 |
| 4,467,794 A | 7/1984 | Kotera et al. | |
| 4,469,835 A | 9/1984 | Laurin | |
| 4,473,369 A | 9/1984 | Lueders et al. | |
| 4,475,900 A | 10/1984 | Popovich et al. | |
| 4,500,788 A | 2/1985 | Kulin et al. | |
| 4,541,829 A | 9/1985 | Munsch et al. | |
| 4,573,980 A | 3/1986 | Karrasch et al. | |
| 4,608,472 A | 8/1986 | Kato | |
| 4,655,762 A | 4/1987 | Rogers | |
| 4,745,950 A | 5/1988 | Mathieu | |
| 4,774,415 A | 9/1988 | Biegel et al. | |
| 4,877,964 A | 10/1989 | Tanaka et al. | |
| 4,878,516 A | 11/1989 | Mathieu | |
| 4,882,496 A | 11/1989 | Bellotti et al. | |
| 4,948,980 A | 8/1990 | Wedekamp | |
| 4,949,723 A | 8/1990 | Wallace et al. | |
| 4,950,230 A | 8/1990 | Kendell | |
| 4,950,260 A * | 8/1990 | Bonaldo | A61M 39/14 604/535 |
| 4,980,374 A | 12/1990 | Steudle et al. | |
| 5,047,011 A | 9/1991 | Caron et al. | |
| 5,057,074 A | 10/1991 | Suzuki et al. | |
| 5,105,853 A | 4/1992 | Lie | |
| 5,147,321 A | 9/1992 | Slonina et al. | |
| 5,190,534 A | 3/1993 | Kendell | |
| 5,221,267 A | 6/1993 | Folden | |
| 5,242,150 A | 9/1993 | Shiffler et al. | |
| 5,336,173 A | 8/1994 | Folden | |
| 5,417,673 A | 5/1995 | Gordon | |
| 5,427,135 A | 6/1995 | Kieper | |
| 5,439,451 A | 8/1995 | Collinson et al. | |
| 5,536,258 A | 7/1996 | Folden | |
| 5,540,668 A | 7/1996 | Wilson et al. | |
| 5,555,908 A | 9/1996 | Edwards et al. | |
| 5,603,902 A | 2/1997 | Maltais et al. | |
| 5,612,001 A | 3/1997 | Matschke | |
| 5,640,690 A | 6/1997 | Kudrna | |
| 5,713,850 A | 2/1998 | Heilmann et al. | |
| 5,714,119 A | 2/1998 | Kawagoe et al. | |
| 5,832,959 A | 11/1998 | Szymczakowski et al. | |
| 5,855,203 A | 1/1999 | Matter | |
| 6,027,489 A | 2/2000 | Galato | |
| 6,120,166 A | 9/2000 | Price | |
| 6,228,332 B1 | 5/2001 | Dunn et al. | |
| 6,245,570 B1 | 6/2001 | Grimm et al. | |
| 6,418,257 B1 | 7/2002 | Nath | |
| 6,461,568 B1 | 10/2002 | Eckhardt | |
| 6,461,569 B1 | 10/2002 | Boudreaux | |
| 6,470,888 B1 | 10/2002 | Matter | |
| 6,485,483 B1 | 11/2002 | Fujii | |
| 6,569,564 B1 | 5/2003 | Lane | |
| 6,592,558 B2 | 7/2003 | Quah | |
| 6,682,507 B2 | 1/2004 | Irish | |
| 6,803,363 B2 | 10/2004 | Polaschegg | |
| 6,834,984 B2 | 12/2004 | Tausch et al. | |
| 7,083,605 B2 | 8/2006 | Miyahara | |
| 7,198,611 B2 | 4/2007 | Connell et al. | |
| 7,232,428 B1 | 6/2007 | Inukai et al. | |
| 7,232,429 B2 | 6/2007 | Moreci | |
| 7,274,847 B2 | 9/2007 | Gowda et al. | |
| 7,452,346 B2 | 11/2008 | Axelsson | |
| 7,497,849 B2 | 3/2009 | Fangrow | |
| 7,806,851 B2 | 10/2010 | Cerasoli | |
| 7,955,295 B2 | 6/2011 | Lee et al. | |
| 8,197,087 B2 | 6/2012 | Sobue et al. | |
| 8,282,829 B2 | 10/2012 | Yu et al. | |
| 8,431,074 B2 | 4/2013 | Neer | |
| 8,478,385 B2 | 7/2013 | Liu et al. | |
| 8,585,681 B2 | 11/2013 | Boenig et al. | |
| 8,641,659 B2 | 2/2014 | Soykan et al. | |
| 8,946,653 B2 | 2/2015 | Victor et al. | |
| 9,295,742 B2 | 3/2016 | Rasooly et al. | |
| 2003/0010927 A1 | 1/2003 | Wedekamp | |
| 2003/0017073 A1 | 1/2003 | Eckhardt et al. | |
| 2004/0195538 A1 | 10/2004 | Raines et al. | |
| 2005/0013729 A1 | 1/2005 | Brown-Skrobot et al. | |
| 2005/0124970 A1 | 6/2005 | Kunin et al. | |
| 2005/0163655 A1 | 7/2005 | Lin et al. | |
| 2005/0258762 A1 | 11/2005 | Beland et al. | |
| 2005/0261621 A1 | 11/2005 | Perez | |
| 2006/0027270 A1 | 2/2006 | Truitt et al. | |
| 2006/0122559 A1 | 6/2006 | Shia et al. | |
| 2006/0147339 A1 | 7/2006 | Hunter et al. | |
| 2006/0163515 A1 | 7/2006 | Ruschke | |
| 2006/0186010 A1 | 8/2006 | Warnack et al. | |
| 2006/0202146 A1 * | 9/2006 | Doyle | A61M 39/26 251/149.1 |
| 2007/0023710 A1 | 2/2007 | Tom et al. | |
| 2007/0176117 A1 | 8/2007 | Redmond et al. | |
| 2007/0179473 A1 | 8/2007 | Masters et al. | |
| 2007/0232989 A1 | 10/2007 | Kitani et al. | |
| 2007/0274879 A1 | 11/2007 | Millikin | |
| 2007/0257953 A1 | 12/2007 | Ziv et al. | |
| 2008/0045884 A1 | 2/2008 | Landherr et al. | |
| 2008/0183126 A1 | 7/2008 | Landherr et al. | |
| 2008/0183127 A1 | 7/2008 | Landherr et al. | |
| 2008/0195031 A1 | 8/2008 | Kitani et al. | |
| 2008/0306454 A1 | 12/2008 | Sikora | |
| 2009/0001720 A1 * | 1/2009 | Cheon | A61M 39/26 285/317 |
| 2009/0012451 A1 | 1/2009 | Sobue et al. | |
| 2009/0149776 A1 | 6/2009 | Adams | |
| 2009/0205664 A1 | 8/2009 | Lyon | |
| 2009/0257910 A1 | 10/2009 | Segal | |
| 2009/0259203 A1 | 10/2009 | Hu et al. | |
| 2009/0289015 A1 | 11/2009 | Levy | |
| 2009/0320316 A1 | 12/2009 | Zakai | |
| 2010/0072399 A1 | 3/2010 | Street et al. | |
| 2010/0072506 A1 | 3/2010 | Bae et al. | |
| 2010/0249586 A1 | 9/2010 | Cocker et al. | |
| 2011/0028915 A1 | 2/2011 | Siopes et al. | |
| 2011/0064608 A1 | 3/2011 | Lee et al. | |
| 2011/0085936 A1 | 4/2011 | Haytman et al. | |

(56) References Cited

U.S. PATENT DOCUMENTS

| | | |
|---|---|---|
| 2011/0165020 A1 | 7/2011 | Tryggvason et al. |
| 2011/0213339 A1 | 9/2011 | Bak |
| 2011/0224624 A1 | 9/2011 | Geller |
| 2012/0053512 A1 | 3/2012 | Muse |
| 2012/0116294 A1* | 5/2012 | Boenig ............... A61M 39/18 604/29 |
| 2012/0161032 A1 | 6/2012 | Arcand et al. |
| 2012/0205825 A1 | 8/2012 | Nagafuji et al. |
| 2012/0206992 A1 | 8/2012 | Stewart |
| 2012/0296151 A1 | 11/2012 | Curtis et al. |
| 2012/0310179 A1 | 12/2012 | Truitt et al. |
| 2012/0321509 A1 | 12/2012 | Bak |
| 2013/0131626 A1 | 5/2013 | Thompson et al. |
| 2013/0204227 A1 | 8/2013 | Bochenko et al. |
| 2013/0323119 A1 | 12/2013 | Alwan |
| 2014/0076454 A1 | 3/2014 | Kjar |
| 2014/0205498 A1 | 7/2014 | Bak |
| 2014/0276215 A1 | 9/2014 | Nelson et al. |
| 2014/0276345 A1 | 9/2014 | Silin |
| 2014/0334974 A1* | 11/2014 | Rasooly ............... A61L 2/10 422/24 |
| 2015/0258230 A1 | 9/2015 | Victor et al. |
| 2015/0352348 A1 | 12/2015 | Murphy-Chutorian et al. |
| 2016/0082138 A1 | 3/2016 | Kermode et al. |

FOREIGN PATENT DOCUMENTS

| | | | |
|---|---|---|---|
| CN | 203408290 U | 1/2014 | |
| EP | 0229786 B1 | 3/1990 | |
| EP | 0163811 B1 | 8/1991 | |
| EP | 2161040 A1 | 3/2010 | |
| EP | 2314802 A2 | 4/2011 | |
| FR | 2799373 | 4/2001 | |
| JP | 2008/68049 | 3/2008 | |
| WO | WO83/02060 A1 | 6/1983 | |
| WO | WO-8302060 A1 * | 6/1983 | ............ A61M 39/16 |
| WO | WO92/19284 A1 | 11/1992 | |
| WO | WO02/074350 A1 | 9/2002 | |
| WO | WO2007/103998 A2 | 9/2007 | |
| WO | WO2008/014437 A2 | 1/2008 | |
| WO | WO2009/094034 A1 | 7/2009 | |
| WO | WO2010/036617 A1 | 4/2010 | |
| WO | WO2011/00787 A1 | 1/2011 | |
| WO | WO2011/143140 A2 | 11/2011 | |
| WO | WO2014/013385 A1 | 1/2014 | |
| WO | WO2015/157662 A1 | 10/2015 | |
| WO | WO2016/044821 A1 | 3/2016 | |
| WO | WO2017/192262 A1 | 11/2017 | |

OTHER PUBLICATIONS

Bak et al.; Dose requirement for UVC disinfection of catheter biofilms; Biofouling: The Journal of Bioadhesion and Biofilm Research; 25(3); pp. 289-296; Apr. 2009.

Bak et al.; Potential in vivo UVC disinfection of catheter lumens: estimation of the doses received by the blood flow outside the catheter tip hole; Photochemistry and Photobiology; 87(2); pp. 350-356; Mar.-Apr. 2011.

Bak et al.; UVC fluencies of preventative treatment of *Pseudomonas aeruginosa* contaminated polymer tubes; Biofouling: The Journal of Bioadhesion and Biofilm Research; 26(7); pp. 821-828; Oct. 2010.

Qamar et al; Clinical outcomes in peritoneal dialysis: Impact of continuous improvement quality initiatives; Advances in Peritoneal Dialysis; vol. 25; pp. 76-79; 2009 (year of pub. sufficiently earlier than effective US filing and any foreign priority date).

Kermode et al.; U.S. Appl. No. 15/301,905 entitled "Connector disinfection system," filed Oct. 4, 2016.

* cited by examiner

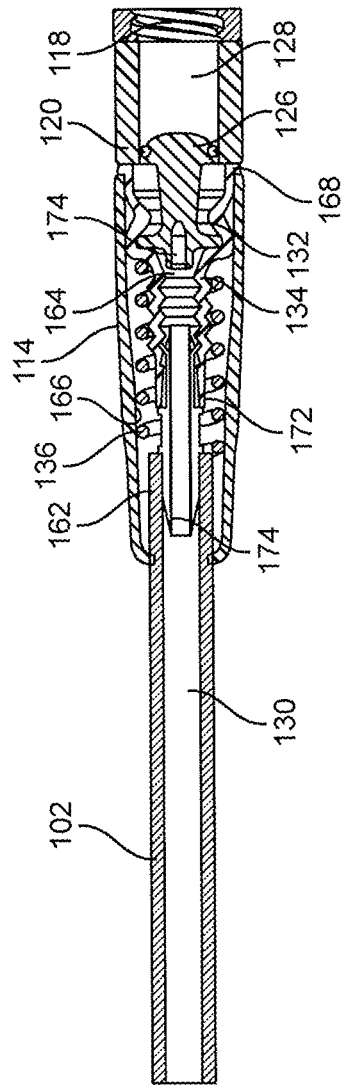
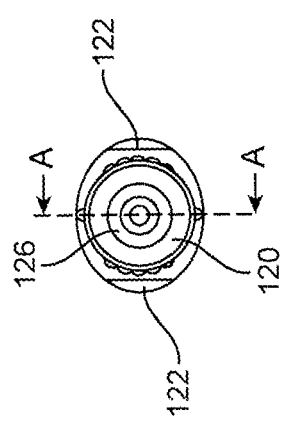
FIG. 4B
FIG. 4A

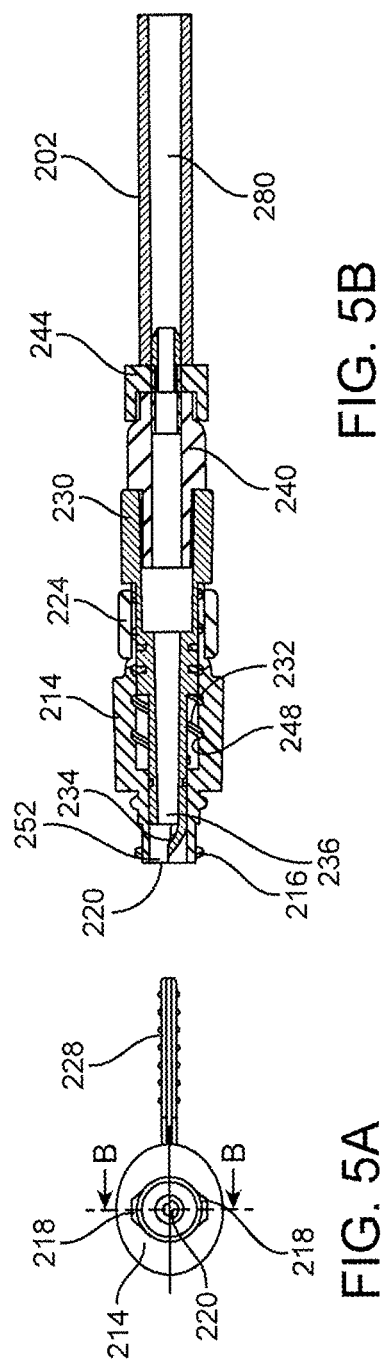

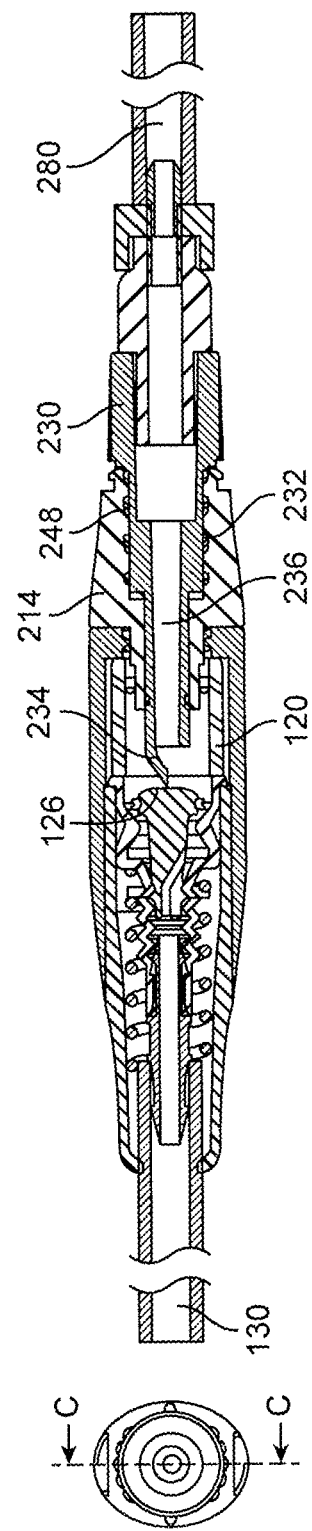

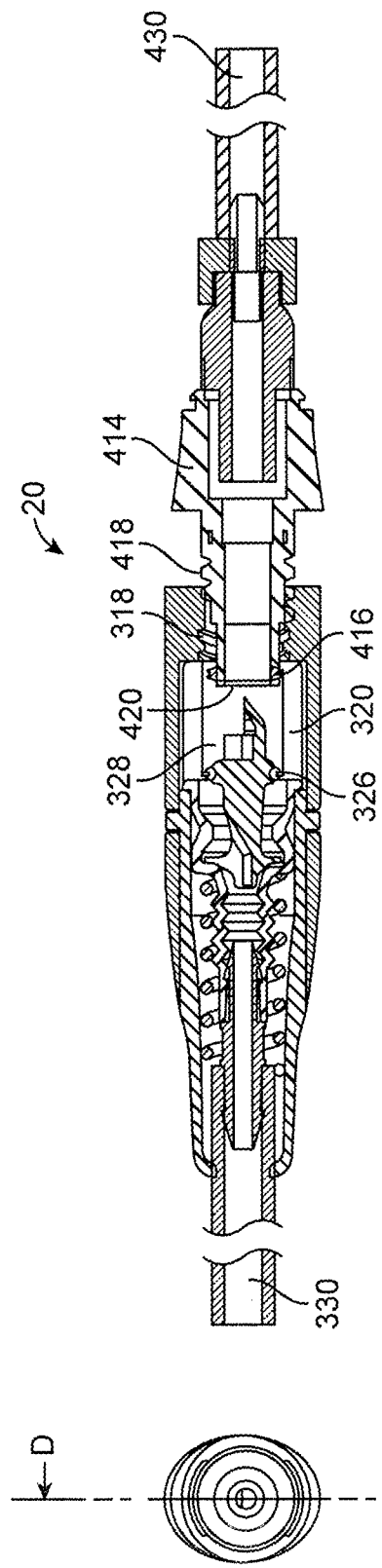

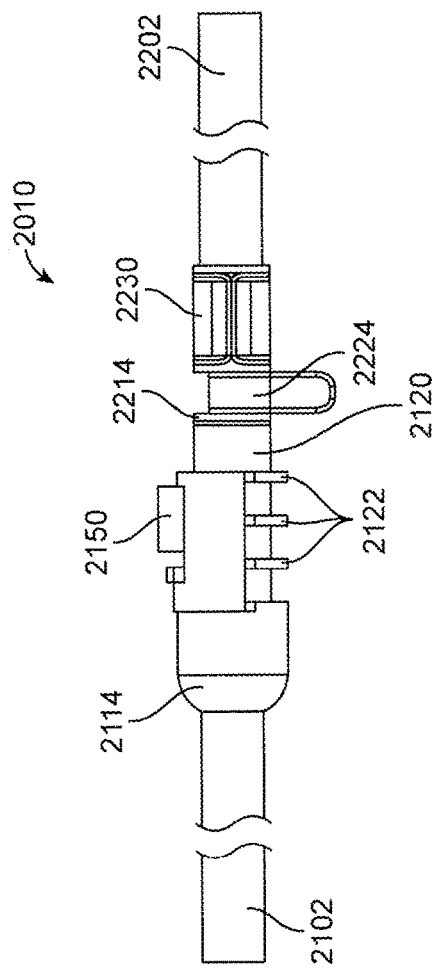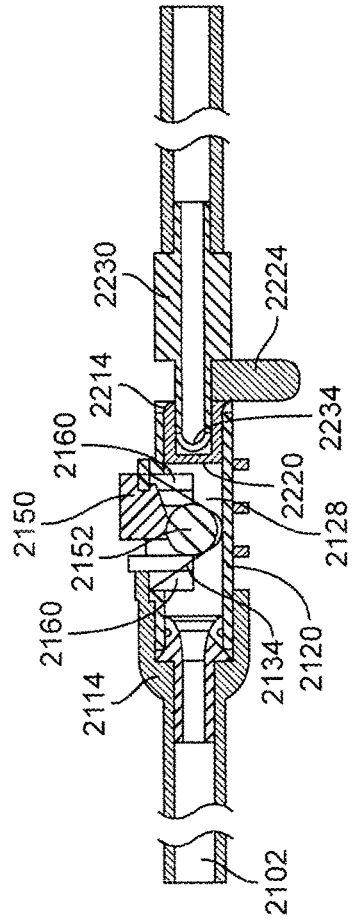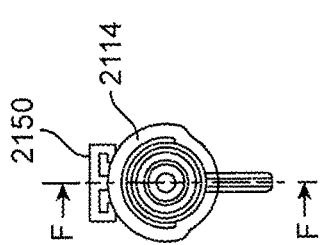

CATHETER CONNECTION SYSTEM FOR ULTRAVIOLET LIGHT DISINFECTION

PRIORITY INFORMATION

This application claims the benefit of U.S. Provisional Patent Application No. 62/135,080, filed Mar. 18, 2015 and U.S. Provisional Patent Application No. 62/238,644, filed Oct. 7, 2015.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD

This application relates generally to sterilization units, more particularly, sterilization of connectors used in a medical application, for example, during peritoneal dialysis (PD).

BACKGROUND

Catheters are commonly used to infuse fluids into or remove them from various locations in the human body. In many cases these catheters are left in place for weeks or months to provide this access. The longer an indwelling catheter provides this communication between the outside and inside of the body the greater the likelihood microbes such as bacteria, fungi, and viruses can migrate into the body and cause an infection. These infections can be very difficult and costly to treat and can result in a high level of morbidity for patients that have a need for this catheterization. Therefore, there is a high need for preventing the migration of microbes through the catheter and into the body.

The opportunity for microbes to enter the catheter occurs each time the connection point between the indwelling catheter and other equipment used for removing or infusing fluids is opened and closed. One way of preventing the migration of microbes through the catheter into the body is to disinfect the connection point each time it is opened and closed. One particular application for disinfecting this catheter connection point is during peritoneal dialysis.

Peritoneal dialysis (PD) can be used as a treatment for patients with severe chronic kidney disease. Fluid is introduced through a tube in the abdomen and flushed out periodically either while the patient sleeps, in automated peritoneal dialysis, or during regular dialysis sessions through the day, as in continuous ambulatory peritoneal dialysis.

As shown in FIG. 1, a patient undergoing peritoneal dialysis can have an indwelling catheter 4 surgically inserted into the abdomen. A transfer catheter 2 can be attached to the indwelling catheter. The transfer catheter can be replaced, in a sterile environment, such as at a clinic, every few months to a year. Between dialysis sessions, the patient wears the transfer catheter against the body. During dialysis sessions, the transfer catheter can be connected to a drain bag to drain the fluid present in the abdomen and a fresh dialysate bag to introduce fluid to the abdomen. The drain bag and dialysate bags can be attached in series or can be attached in parallel using a Y-shaped solution set catheter 6. Prior to each treatment, the patient connects the tip of the transfer catheter to a new dialysis solution set catheter using rigorous aseptic techniques to maintain sterility. The aseptic technique include the patient and anyone around them wearing a mask, closing doors and windows, turning off fans, and thoroughly washing hands for 2 minutes. Then the patient typically scrubs the opening of the transfer catheter with alcohol, iodine, or a similar antiseptic agent prior to connecting the catheters. The same sterile technique must be employed when disconnecting the catheters as well. If sterility is compromised at any time, the component being used must be replaced and the whole process started again. Once the patient feels confident enough to perform the procedure at home unattended, and after many months of practice, the time to disinfect, connect and start PD takes approximately 20-30 minutes.

This is obviously a complicated and time-consuming process that is highly reliant on patient compliance. If a patient fails to adhere to any of the strict steps of the sterilization procedure, he or she faces a greatly increased risk of a serious infection that targets the peritoneal cavity, commonly referred to as peritonitis. This type of internal infection, if not caught early, may leads to sepsis and death of the patient. Typically, PD patients experience a 50% chance of infection during the first 12 to 18 months and experience 15% mortality/yr directly related to the infection. In addition to seriously endangering the patient's health, infections in peritoneal dialysis are also very costly to treat. The average total charges form a peritonitis hospital stay are roughly $50,000 dollars and the entire annual cost to the healthcare system is around $1.5 billion. Given that the noncompliance rate for a standard PD procedure is around 30%, there is a huge need to help reduce the health and financial burdens of infection.

Ultraviolet (UV) disinfection systems are known in the art. U.S. Pat. Nos. 4,882,496; 7,834,328; 4,620,845; 6,461,568 and U.S. Publication Nos. 2005/0013729 and 2007/0274879, the disclosures of which are incorporated by reference herein in their entireties, describe such systems. However, such systems can be cumbersome, making them difficult for a patient to use. Additionally, such systems tend to rely on UV disinfection for complete disinfection, which can, in the absence of proper components and connectors, limit the effectiveness of the disinfection.

SUMMARY OF THE DISCLOSURE

In some embodiments, an ultraviolet (UV) catheter connection disinfection system is provided. The system comprises a first connector comprising a UV transparent region at a first end of the first connector and a sealing plunger positioned proximal to the first end of first connector; a second connector comprising a leading membrane surface and a sealing surface for sealing against the UV transparent region at a first end of the second connector; a piercing member configured to pierce the leading membrane surface; and a deflector configured to deflect the sealing plunger into a flow position, wherein the first end of the second connector is configured to mate with the first end of the first connector in a first disinfection position in which the leading membrane surface is intact and the sealing plunger is blocking flow through the first connector and a second flow position in which the leading membrane surface is punctured by the piercing member and the sealing plunger is deflected into the flow position by the deflection member.

In some embodiments, in the disinfection position a small volume disinfection zone is bounded by the leading membrane surface, and inner surface of the UV transparent region, and the sealing plunger. The sealing surface can comprise at least one of an o-ring, a wiper shaped blade, and a spring energized seal. In some embodiments, the sealing surface comprises at least one of silicone, butyl rubber, PTFE, and neoprene. The leading membrane surface can comprise at least one of metallic foil and plastic foil. In some embodiments, the UV transparent region comprises at least one of quartz glass, cyclic olefin copolymer, and TPX (polymethylpentene polyolefins). The system can further comprise a stop configured to prevent the system from inadvertently moving from the disinfection to the flow position. In some embodiments, the stop comprises a clip. The system can further comprise a spring maintaining the plunger seal in a sealing position within the UV transparent region. In some embodiments, a second end of the second connector is configured to connect to a tubular member through a sealed connector, the tubular member removable from the second connector while maintaining the seal at the second end of the second connector. The sealed connector can comprise a needleless connector. The sealed connector can comprise a luer connector. In some embodiments, the luer connector is removed along with the tubular member. The first connector can be configured to connect to an indwelling catheter. The second connector can be configured to connect to a solution set catheter. In some embodiments, the second connector comprises the piercing member. The piercing member can serve as the deflector. The first connector can comprise the piercing member. The sealing plunger can comprise the piercing member. In some embodiments, the first connector and the second connector comprise threads to hold the connectors together. In some embodiments, the sealing surface comprises the joining of the UV transparent region and the first end of the second connector. The first connector can comprise a sealing actuator configured to advance the sealing plunger against an opening of the UV transparent region. In some embodiments, the sealing plunger and the leading membrane surface are resealable. In some embodiments, the sealing plunger and the leading membrane surface are single use components. In some embodiments, the sealing plunger is resealable and the leading membrane surface is a single use component. In some embodiments, the sealing plunger is a single use component and the leading membrane surface is resealable.

In some other embodiments, a method of ultraviolet (UV) disinfection is provided. The method comprises connecting a first end of a first connector with a second end of a second connector such that the connectors are in a disinfection position, the first connector comprising a lumen formed using a UV transparent region; a first sealing member positioned in the UV transparent region and blocking flow through the first connector; the second connector comprising a second sealing member configured to sealingly engage a surface of the UV transparent region; a leading membrane surface separating a lumen of the second connector from the lumen of the first connector; and a piercing member; exposing the UV transparent region to UV light; advancing the second connector with respect to the first connector; piercing the leading membrane surface with the piercing member; and deflecting the first sealing member to allow flow between the first connector lumen and the second connector lumen.

In other embodiments, another method of UV disinfection is provided. The method comprises connecting a distal end of a transfer catheter connector with a proximal end of a solution set catheter connector such that the connectors are in a disinfection position, the transfer catheter connector comprising a lumen having a UV transparent region at its distal end; a first sealing member positioned in the UV transparent region and blocking flow through the transfer catheter connector; the solution set catheter connector comprising a second sealing member configured to sealingly engage a surface of the UV transparent region; a leading membrane surface separating a lumen of the solution set catheter connector from the lumen of the transfer catheter connector; and a piercing member; exposing the UV transparent region to UV light; advancing the transfer catheter connector with respect to the solution set connector so that the connectors are in a flow position; piercing the leading membrane surface with the piercing member; and deflecting the first sealing member to allow flow between the transfer catheter connector lumen and the solution set catheter connector lumen. Advancing the transfer catheter connector with respect to the solution set connector comprises turning the connector relative to one another.

In some embodiments, the method further comprises disengaging a stop prior to advancing the transfer catheter connector relative to the solution set catheter connector. Disengaging the stop can comprise removing a c clip. In some embodiments, the method further comprises flowing fresh dialysate from a solution set catheter connected to the solution set catheter connector to the transfer catheter connector. The method can further comprise removing the solution set catheter from the solution set catheter connector while maintaining a seal at a distal end of the solution set catheter connector.

In some embodiments, a UV disinfection system for use during peritoneal dialysis is provided. The system comprises a transfer catheter connector comprising a UV transparent region at a distal end of the connector; a valve positioned at a proximal end of the UV transparent region; and a piercing member positioned within the valve; a solution set connector comprising a lumen configured to be fluidly connected to the solution set tubing, a proximal end of the lumen sealed with a barrier, the lumen comprising a seal around a portion of the lumen, wherein a portion of the UV-transparent region is configured to be inserted within a portion of the solution set connector into a first disinfection position in which the barrier is intact and a second flow position in which the barrier is punctured by the piercing member.

The valve can allow passage of the piercing member therethrough and be configured to return to a sealed state upon retraction of the piercing member. The transfer catheter can comprise threads configured to mate with threads on the solution set connector. In some embodiments, the UV-transparent region comprises quartz. The piercing member can be configured to extend through the valve upon deflection of the valve towards the piercing member. IN some embodiments, the transfer catheter connector comprises a stop configured to interact with a mating feature on the solution set connector.

In some embodiments, a UV disinfection system is provided. The system comprises a transfer catheter connector comprising a lumen formed using an UV transparent region at a distal end of the connector; a valve positioned at a proximal end of the UV transparent region and within the lumen; and a piercing member positioned within the connector and separated from the lumen by the valve; a solution set connector comprising a lumen configured to be fluidly connected to the solution set tubing, an insertion tube sized for positioning within the UV transparent region, a barrier over a proximal opening of the insertion tube, a seal around an exterior portion of the insertion tube sized for sealing engagement with an interior surface of the UV transparent region, wherein a portion of the UV-transparent region is configured to be inserted within a portion of the solution set connector into a first disinfection position in which the barrier is intact and a second flow position in which the barrier is punctured by the piercing member.

In some embodiments, a method of UV disinfection is provided. The method comprises inserting a distal end of a transfer catheter connector into a proximal end of a solution set connector such that the connectors are in a disinfection position, the transfer catheter connector comprising a lumen formed using an UV transparent region at a distal end of the connector; a valve positioned at a proximal end of the UV transparent region and within the lumen; and a piercing member positioned within the connector and separated from the lumen by the valve, and the solution set connector comprising a lumen configured to be fluidly connected to the solution set tubing, an insertion tube sized for positioning within the UV transparent region, a barrier over a proximal opening of the insertion tube, a seal around an exterior portion of the insertion tube sized for sealing engagement with an interior surface of the UV transparent region; placing the transfer catheter connector and the solution set connector into a UV disinfection unit; activating the disinfection unit; further inserting the transfer catheter connector into the proximal end of the solution set connector such that the connectors are in a flow position; piercing the barrier with the piercing member; and opening a transfer catheter clamp to allow flush of spent dialysate.

In some embodiments, further inserting the transfer catheter connector into the proximal end of the solution set connector such that the connectors are in a flow position comprises turning the connectors relative to one another about 1 full turn. In some embodiments, inserting a distal end of a transfer catheter connector into a proximal end of a solution set connector such that the connectors are in a disinfection position comprises turning the connectors relative to one another about ¼ turn. Inserting a distal end of a transfer catheter connector into a proximal end of a solution set connector such that the connectors are in a disinfection position can comprise inserting the distal end of the transfer catheter connector until a stop on the transfer catheter connector engages with a mating feature on the solution set connector. In some embodiments, further inserting the transfer catheter connector into the proximal end of the solution set connector such that the connectors are in a flow position first comprises disengaging the stop from the mating feature.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4a is an illustration of an end view of an embodiment of the transfer catheter of a catheter connection system.

FIG. 4b is an illustration of a cross section view of an embodiment of the transfer catheter from FIG. 4a through line A-A.

FIG. 5a is an illustration of an end view of an embodiment of the solution set catheter of a catheter connection system.

FIG. 5b is an illustration of a cross section view of an embodiment of the solution set transfer catheter from FIG. 5a through line B-B.

FIG. 6b is an illustration of a detailed view of an embodiment of the catheter connection system from FIG. 6a.

FIG. 7b is an illustration of a detailed view of an embodiment of the catheter connection system from FIG. 7a.

FIG. 7c is an illustration of an end view of an embodiment of the catheter connection system.

FIG. 7d is an illustration of a cross section view of an embodiment of the catheter connection system from FIG. 7c through line C-C.

FIG. 9b is an illustration of an end view of an embodiment of the catheter connection system from FIG. 9a.

FIG. 9c is an illustration of a cross section view of an embodiment of the catheter connection system from FIG. 9b through line D-D with the connection sealed to prevent fluid flow before disinfection.

FIG. 10b is an illustration of an end view of an embodiment of the catheter connection system from FIG. 10a.

FIG. 11a is an illustration of a detailed view of yet another alternate embodiment of the catheter connection system.

FIG. 11b is an illustration of an end view of an embodiment of the catheter connection system from FIG. 11a.

FIG. 11c is an illustration of a cross section view of an embodiment of the catheter connection system from FIG. 11b through line F-F.

FIG. 12b is an illustration of an end view of an embodiment of the catheter connection system from FIG. 12a.

DETAILED DESCRIPTION

Figure 1:
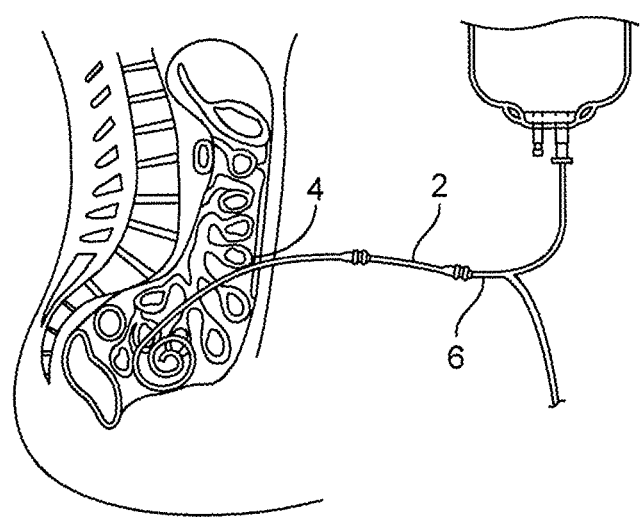
FIG. 1 is an illustration of a conventional peritoneal dialysis setup.
Figure 2:
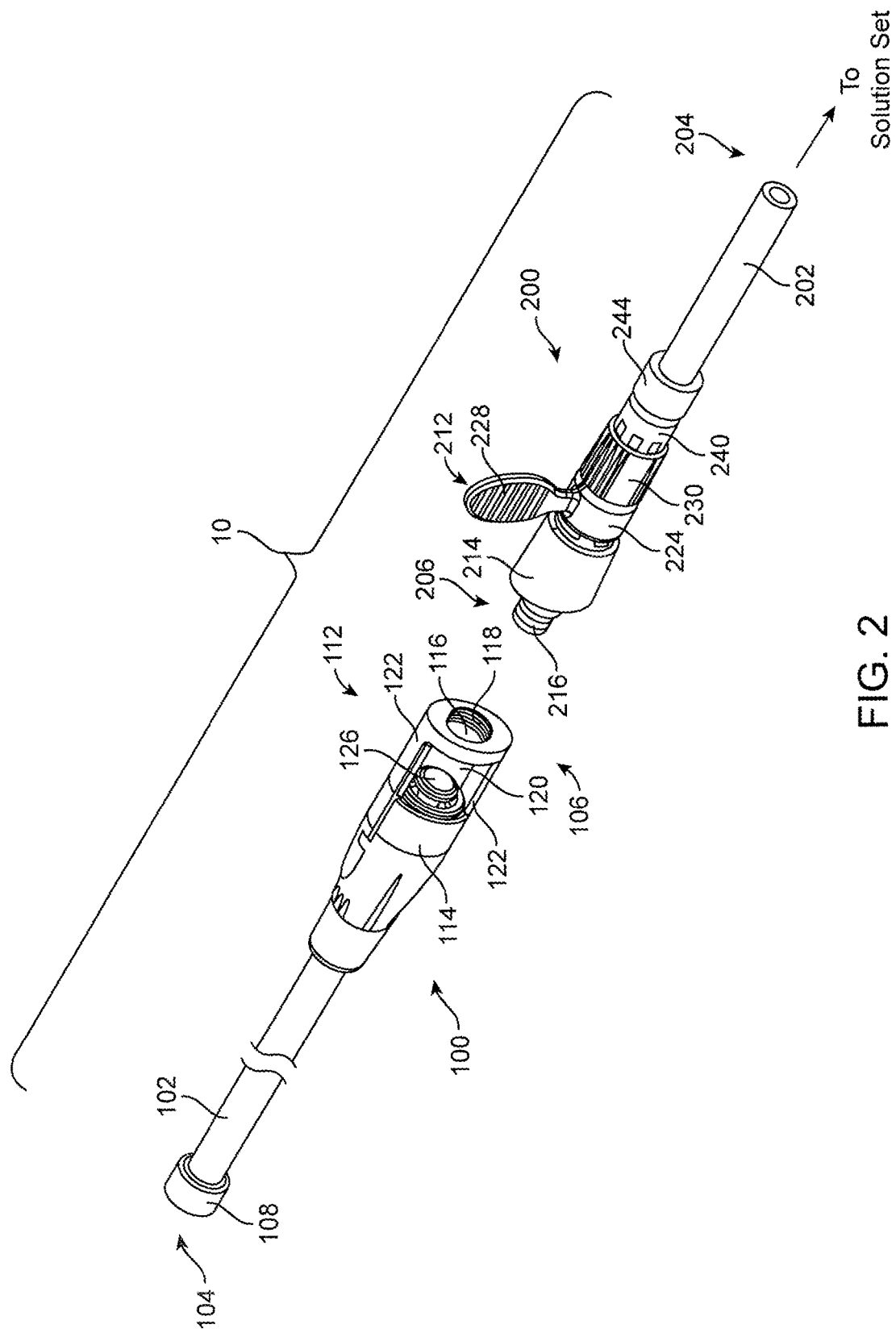
FIG. 2 is an illustration of an embodiment of a catheter connection system.
Figure 3:
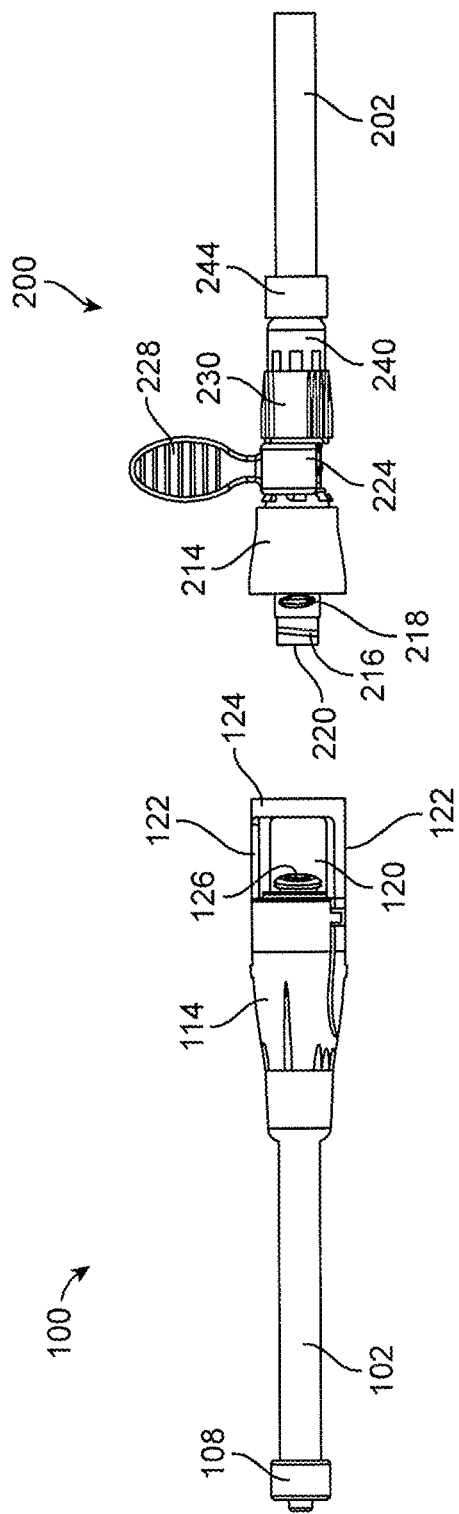
FIG. 3 is an illustration of a side view of an embodiment of a catheter connection system.

Embodiments of the catheter connection system disclosed herein can be used by peritoneal dialysis (PD) patients. FIG. 2 illustrates an embodiment of a catheter connection system 10 that can be used like the transfer catheter 2 and solution set catheter 6 of FIG. 1. The transfer catheter 100 of the catheter connection system 10 of the current invention comprises a tubular body 102, a first end 104 and a second end 106. The transfer catheter 100 comprises a first connector 108 positioned at or near the first end 104, and a second connector 112 positioned at or near the second end 106. Referring also to FIG. 3, the second connector 112 comprises a connector body 114, an end retainer 124, and one or more struts 122 which connect the end retainer 124 to the connector body 114. A UV transparent section 120 is constrained between the connector body 114, the end retainer 124, and the struts 122. The struts 122 are configured to allow UV light to be directed to the UV transparent section 120 from one or more directions without creating any shadows or blocking the UV light from covering the entire transparent section 120. FIG. 2 shows the second connector 112 comprising two struts, but other configurations are also possible. For example, the second connector 112 can comprise 1, 3, 4, 5, or more struts 122. In some embodiments, the struts 122 comprise square edges, as shown in FIG. 2. Other configurations are also possible. For example, the struts 122 may comprise chamfered edges.

Inside the UV transparent section 120 is a sealing plunger 126 which can be actuated to seal off the inside of the UV transparent section 120 from the inside of the connector body 114 and the rest of the fluid path as will be explained in detail below.

The solution set catheter 200 of the catheter connection system 10 comprises a tubular body 202, a first end 204, and a second end 206. The solution set catheter 200 comprises a male connector 212 positioned at or near the second end 206, and is connected to a solution set (not shown) at the first end 204. The male connector 212 is configured to connect to the second connector 112 of the transfer catheter 100. The male connector 212 comprises a connector hub 214, a leading membrane surface 220, a sealing surface 216 and one or more securing threads 218. The leading membrane surface 220 is configured to be easily positioned inside the UV transparent section 120 of the transfer catheter 100, the sealing surface 216 is configured to seal against the inside of the UV transparent section 120 of the transfer catheter 100 and the securing thread 218 is configured to engage with the threads 118 on the inside of the end portion 124 of the transfer catheter 100 to provide a means for securely attaching the solution set catheter 200 to the transfer catheter 100.

The sealing surface 216 can comprise any one of a number of sealing methods well known to those skilled in the art, including, but not limited to, one or more o-rings, wiper shaped blades, spring energized seals, etc. The sealing material of the sealing surface 216 can be any number of sealing materials well known to those skilled in the art including, but not limited to silicone, butyl rubber, PTFE, neoprene, etc. The leading membrane surface 220 can comprise any number of sealing materials well known to those skilled in the art including, but not limited to, metallic or plastic foil and it can be attached to the connector hub 214 via adhesive, dip coating, over-molded, etc. The UV transparent section can comprise any number of UV-transparent substances known to those skilled in the art, such as, but not limited to, quartz glass, cyclic olefin copolymer (e.g., Topas®), and Mitsubishi chemicals TPX (polymethylpentene polyolefins).

The solution set catheter 200 also comprises a c clip 224, a barb hub 230, a needleless connector 240 and a male luer connector 244. The c clip 224 is positioned between the connector hub 214 and the barb hub 230 and prevents relative motion between the barb hub 230 and the connector hub 214 while it is in place. Other mechanisms for preventing relative motion between the barb hub 230 and the connector hub 214 are also possible (e.g., mating protrusions/recesses on the two connectors). The needleless connector 240 and the male luer connector 244 provide a means of selectively attaching and providing fluid flow between the tubular body 202 to the barb hub 230 as will be explained further herein. The needleless connector 240 and male luer 244 can be any one of a number of readily available connectors that are available from numerous suppliers such as Qosina.

Referring now to FIG. 4b, the cross section of the connector body 114 is shown to contain the sealing plunger 126, a flexible accordion seal 134, a compression spring 136 and the distal end 162 of the tubular body 102. One end of the compression spring 136 is constrained by the inside 166 of the connector body 114 and the other end is pushing against the flexible accordion seal 134. The flexible accordion seal 134 in turn presses against a piston 132 that is part of the sealing plunger 126 and opposite the sealing edge of the sealing plunger 126. In this manner, the compression spring 136, absent any other input, maintains the sealing plunger 126 position inside the UV transparent section 120 and isolates the lumen 130 of the tubular body 102 and the inside 164 of the flexible accordion seal 134 from the inside of the UV transparent section 120. This isolation provides a small controlled volume 128 of the inside of the UV transparent section that is potentially exposed to microorganisms when the second connector 112 is not connected to the solution set connector 212. This small controlled volume 128 can serve as the disinfection zone of the connector system. The volume of the disinfection zone 128 can be about 0.25-0.55 cc, for example about 0.4 cc. Resilient members other than compression springs can also be used to maintain the sealing plunger 126 position inside the UV transparent region 120. The distal end 168 of the flexible accordion seal 134 can also be constrained between the connector body 114 and the UV transparent section 120 to provide a fluid tight connection between them. The proximal end 172 of the flexible accordion seal 134 can be connected directly to the tubular body 102 or can be connected to the tubular body 102 using a standard hose barb connector 174. In either manner of connection, an enclosed fluid pathway is provided from the second end 106 of the second connector 112 to the lumen 130 of the tubular body 102. A groove 174 can also be provided in the piston 134 to ensure that fluid can flow past the piston when it is compressed against the flexible accordion seal 134.

Referring now to FIG. 5b, the cross section of the connector hub 214 is shown with internal threads 248 which are configured to receive the external threads 232 of the barb hub 230. The end of the hollow barb hub 236 is also shown with a piercing member 234 positioned inside of the leading membrane surface 220. It can be seen that there is a continuous enclosed fluid pathway from inside face 252 of the leading membrane surface 220 through the inside of the connector hub 214, the barb hub 230, the needleless connector 240 and the male luer 244 to the lumen 230 of the tubular body 202. When the sterile solution set packaging (not shown) is opened the leading membrane surface 220 maintains the sterility of this fluid pathway as there are no openings for microorganisms.

Figure 6A:
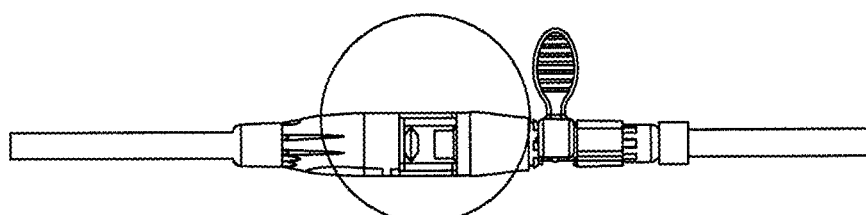
FIG. 6a is an illustration of a side view of an embodiment of a catheter connection system.
Figure 6B:
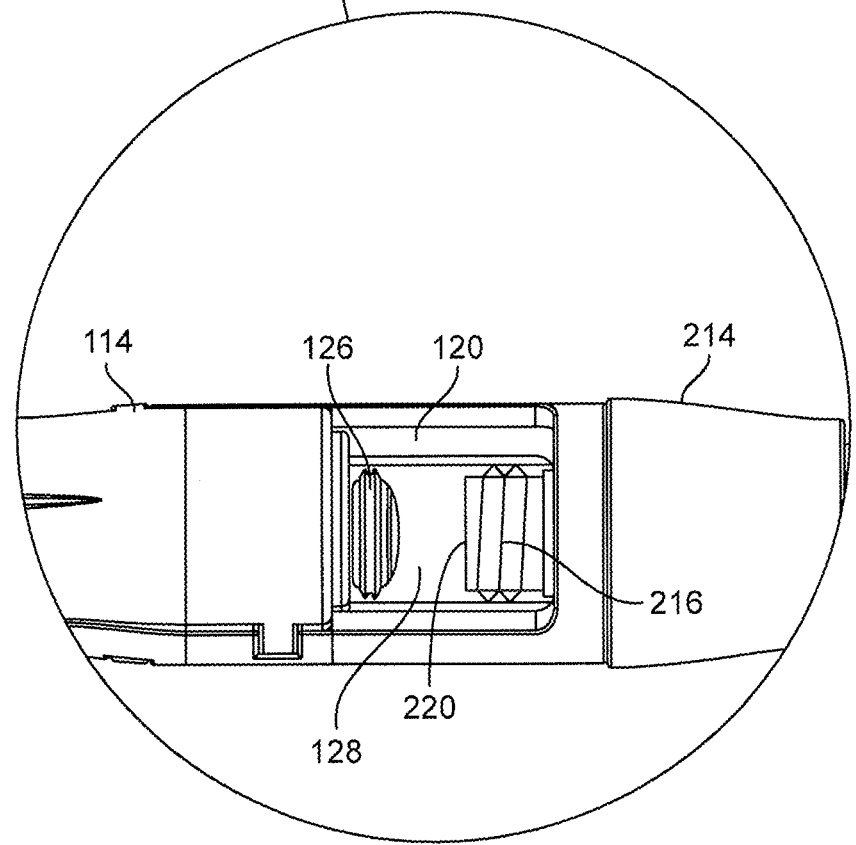
Figure 7A:
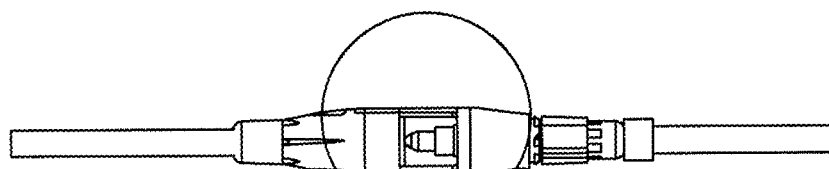
FIG. 7a is an illustration of a side view of an embodiment of a catheter connection system.
Figure 7B:
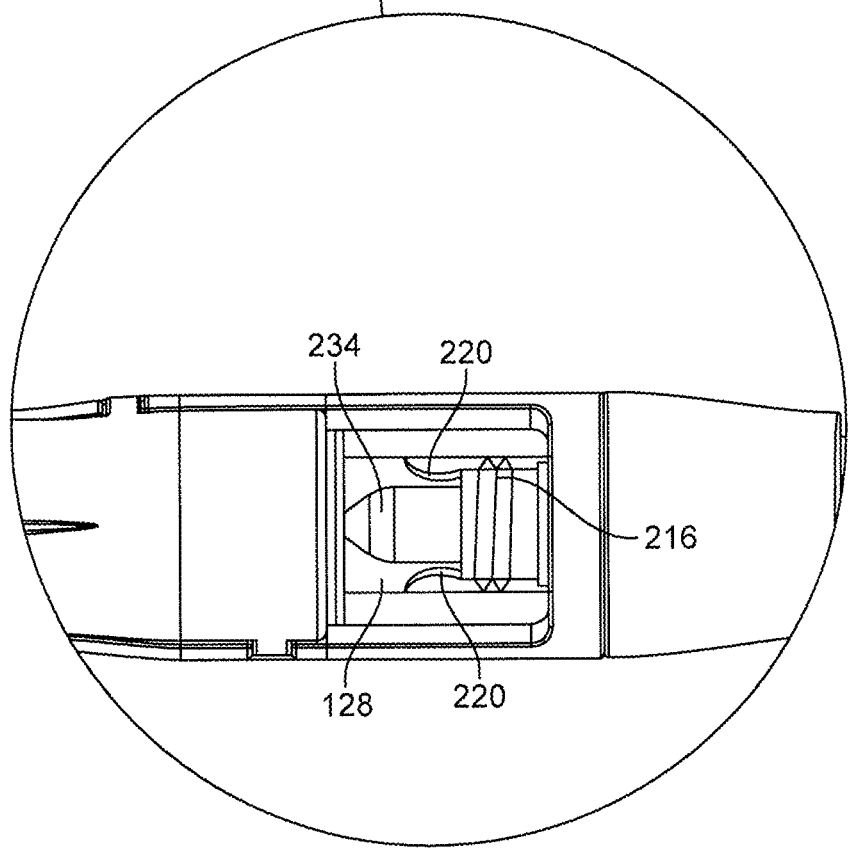

FIGS. 6a and 6b show the transfer catheter 100 connected to the solution set catheter 200. The sealing surface 216 of the solution set catheter 200 is inserted inside the UV transparent section 120 of the transfer catheter 100 and seals against the inner surface, the securing threads 218 (see FIG. 3) of the connector hub 214 engage with the threads 118 of the end retainer 124 of the second connector 112 to maintain the connection of the solution set catheter 200 to the transfer catheter 100. In this configuration, the UV transparent section 120, the sealing surface 216 and the sealing plunger 126 create a small contained volume 128 that is isolated from the outside and from both the transfer catheter 100 inner lumen 130 and the solution set catheter 200 inner lumen 280. This small contained volume 128 comprises all of the inner space that may have been exposed to microorganisms prior to the connection; and it provides a UV-transparent pathway for UVC light to penetrate and kill any microorganisms that may have contaminated the space or the end of the solution set catheter 200 before the connection was made (including the leading membrane surface 220 and any other portion of the connector hub 214 that is in between the leading membrane surface 220 and the sealing surface 216). With this configuration, it is very easy for the user to place the catheter connection system 100 into a UVC generating apparatus (not shown) for delivery of UVC to the disinfection zone 128 to kill any contamination from microorganisms. Alternately the user can direct UVC light into the disinfection zone 128 using an appropriate UVC light apparatus without first placing the catheter connection system 100 into the UVC apparatus. Exemplary UV light apparatuses are described in U.S. application Ser. No. 14/857,522, filed Sep. 17, 2015, entitled "Ultraviolet Disinfection Unit" and International Application No. PCT/US15/25352, filed Apr. 10, 2015, and entitled "Connector Disinfection System".

Referring to FIGS. 7a-7d, the catheter connection system 10 is shown without the c clip 224 and with the barb hub 230 advanced towards the transfer catheter 100. The c clip 224 can be easily removed from the catheter connection system 10 by the user by grasping and pulling the tab 228.

In this embodiment, the barb hub is advanced by rotating wherein the external threads 232 of the barb hub 230 engage the internal threads 248 of the connector hub 214. It will be obvious to those skilled in the art that the use of threads and a rotating motion are just one of many possible means for advancing the barb hub 230 relative to the connector hub 214. Any means can be used in the current invention for advancing the barb hub 234 relative to the connector hub 214 including but not limited to a straight axial movement, without departing from the current invention. For example, in some embodiments, axial motion can be used to move the barb hub 234 relative to the connector hub 214. When advanced, the piercing member 234 (e.g., barb) of the barb hub 230 penetrates the leading membrane surface 220 and creates an opening in the leading membrane surface through which fluid can flow. In the same manner of advancing the barb hub 230 relative to the connector hub 214 and penetrating the leading member surface 220 with the piercing member 234, the advancing piercing member 234 then applies a force on the sealing plunger 126 to overcome the force from the compression spring 136 and advance the sealing plunger 126 out of the UV transparent section 120. In this manner, the small contained volume 128 that was previously isolated (by the UV transparent section 120, sealing plunger 126, and sealing surface 216) and disinfected from all microorganisms by UVC light is now open for fluid flow from the inner lumen 130 of the transfer catheter 100 to the inner lumen 280 of the solution set catheter 200. The flow of fluid from one catheter to the other is not constrained to one direction only and can flow in either direction in the configuration shown in FIGS. 7a-7d.

With the catheter connection system 10 described above, a patient can make a connection to a transfer catheter 100 with a new solution set catheter 200 as is done in the typical PD procedure without the need to go through all the numerous contamination prevention steps as are typically required with the current standard of care. Rather than following those time consuming steps with the catheter connection system 10 of the current invention, the patient can quickly and easily make the connection as described herein, then disinfect the small contained volume 128 using UVC light, and then open the small contained volume 128 by penetrating the seal on the solution set catheter 200 and opening the sealing plunger 126 on the transfer catheter 100 in order to complete the fluid exchange needed for the PD procedure. The catheter connection system 10 both greatly reduces the number of steps needed for PD and greatly increases the efficacy of the disinfection at the connection, the combination of which reduces the complexity and increases the safety of PD.

Figure 8:
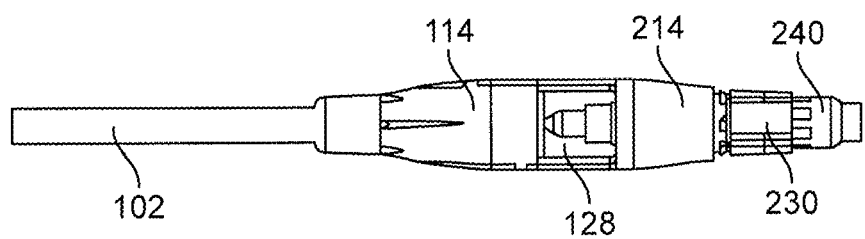
FIG. 8 is an illustration of a side view of an embodiment of a catheter connection system.

After the fluid exchange, it is typical for the solution set catheter 200 to be disconnected from the transfer catheter 100; then the solution set catheter 200 and used solution set are discarded and the second end 106 of the transfer catheter 100 is capped to reduce the chance of microorganisms entering the inner lumen 130. Between the steps of disconnecting the solution set catheter 200 and capping the transfer catheter 100 there is another opportunity for microorganisms to enter the inner lumen 130. Referring to FIG. 8, with the catheter connection system 10 of the current invention, the solution set catheter 200 is not completely disconnected from the transfer catheter 100 after fluid exchange. Rather, the male luer connector 244 and attached tubular body 202 are disconnected from the needleless connector 240 and they are then discarded along with the used solution set. As is well known by those skilled in the art the needleless connector 240 has a seal septum (not shown) which seals the needleless connector 240 and therefore the inner lumen 130 of the catheter connection system 10 as the male luer 244 is removed preventing any contamination on the inner lumen 130 by microorganisms. The remainder of the solution set catheter 200 is left attached to the transfer catheter 100 until the next PD procedure is needed. At that time, the solution set catheter 200 is disconnected from the transfer set catheter 100 by counter rotating the connector hub 214. As the connector hub 214 moves relative to the transfer catheter 100 the piercing member 234 moves relative to the sealing plunger 126 and the sealing plunger 126 reenters the UV transparent section 120 sealing off the inner lumen 130. It will be obvious to those skilled in the art, that the relative positions of the sealing surface 216, the sealing plunger 126 and the piercing member 234 can be configured to ensure that the sealing plunger 126 reenters the UV transparent section 120 and seals it from the inner lumen 130 before the sealing surface 216 exits the other end of the transparent section 120 to ensure that no microorganisms can enter through the UV transparent section 120 and into the inner lumen 130. In this manner, the inner lumen 130 of the transfer catheter 100 is only exposed to potential air and or touch contamination by microorganisms at the beginning of each PD procedure when the solution set catheter 200 is disconnected.

The use of the needleless connector 240 and male luer connector 244 for disconnecting the solution set from the solution set catheter 200 is not the only manner to leave the solution set catheter 200 attached to the transfer catheter 100 to prevent opening the connection and creating the possibility for microorganism contamination at the end of the PD procedure. U.S. Pat. No. 8,038,643 discloses one possible alternate method that includes a connector system whereby a plug is advanced into the first end 204 of the solution set catheter 200 sealing the inner lumen 280 prior to disconnecting the solution set catheter 200 from the used solution set. This method can be also used prevent contamination of the inner lumen space of the current invention. Those skilled in the art will know of methods, other than those described herein for, without departing from the current invention, disconnecting a portion of the solution set catheter 200 from the catheter connection system 10 of the current invention without opening the connection between the transfer catheter 100 and the solution set catheter 200, or otherwise allowing potential contamination by microorganisms of the inner lumen 130.

In some embodiments, the sealing plunger of the transfer catheter connector is a reusable (resealable) element. In some embodiments, the sealing plunger is a single use component, and is replaced between uses. The leading membrane surface can also be a reusable or resealable element. In some embodiments, the leading membrane surface is a single use component.

It will be obvious to those skilled in the art that the current invention is not limited to use in just PD procedures, but can be applied to any procedure where there is an indwelling catheter line going into the body where periodic connection and disconnections need to be done to the external end of the indwelling catheters for the purpose of infusing or removing fluid from the body through the indwelling catheter. Such procedures include Foley catheters placed in the bladder, intravascular lines placed either peripherally or centrally into the vascular system, transparenteral nutrition tubes, esophageal or tracheal tubes and the like. In any of these procedures the potential for contamination of the inner region of the body that the catheter line or equivalent is placed can be reduced by use of the current invention.

Figure 9A:
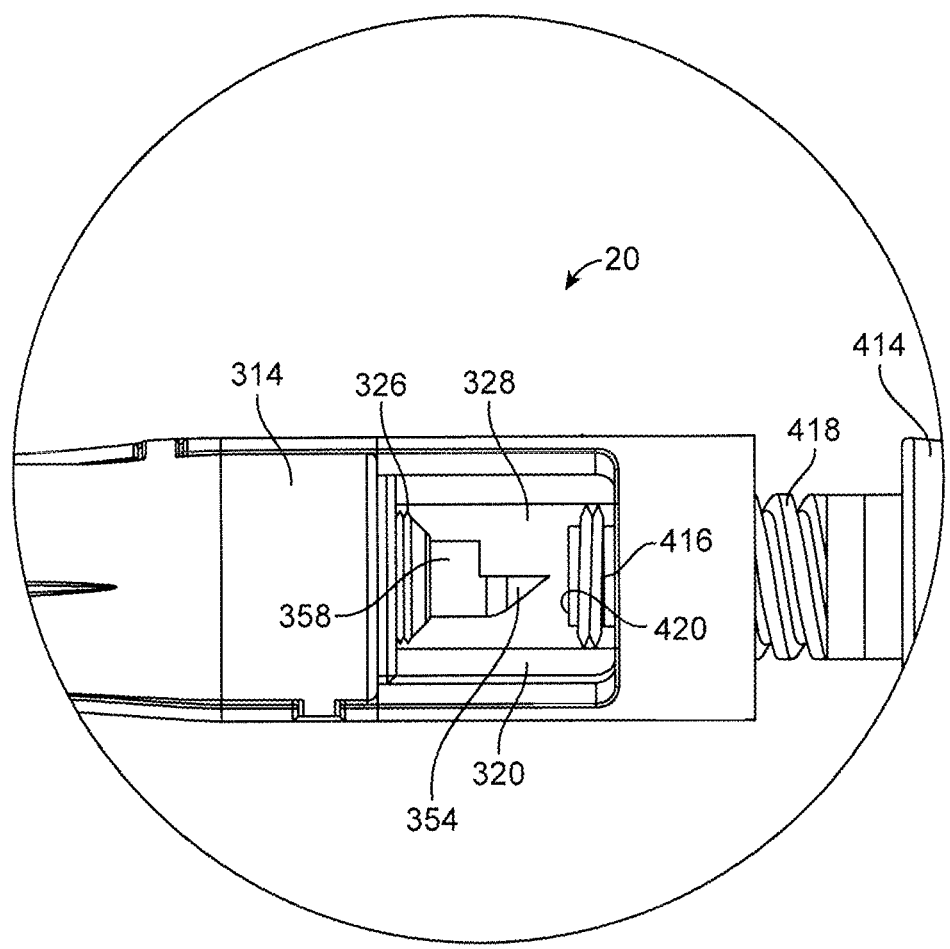
FIG. 9a is an illustration of a detailed view of an alternate embodiment of the catheter connection system.
Figure 9D:
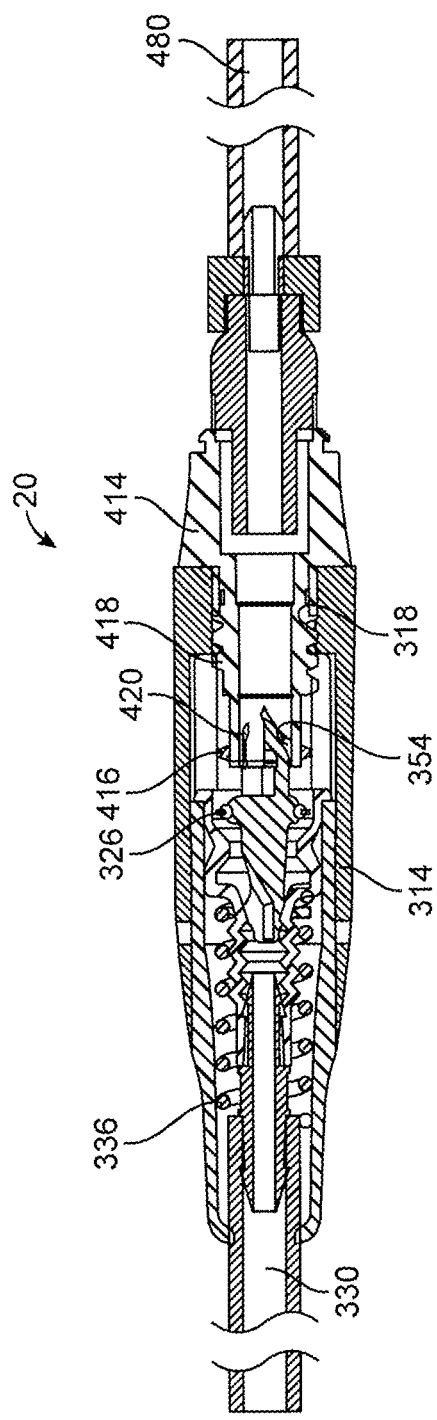
FIG. 9d is an illustration of a cross section view of an embodiment of the catheter connection system from FIG. 9b through line D-D with the connection unsealed to allow fluid flow after disinfection.

The above description describes just one particular embodiment of the current invention. There are many other embodiments possible without departing from the intention of the current invention. One alternate embodiment is show in FIGS. 9a-9c. The catheter connection system 20 of this embodiment includes a sealing plunger 326 that is configured with a piercing member 354. In this embodiment, the connector hub 414 of the solution set catheter engages with the UV transparent section 320 sufficiently for the sealing surface 416 to seal against the inside of the UV transparent section 320 and the leading membrane surface 420 of the connector hub 414 along with the sealing plunger 326 and the UV transparent section 320 create a small contained volume 328. After the small contained disinfection zone volume 328 has been disinfected with UVC light the connector hub 414 is further advanced into the UV transparent section 320 by rotating which advances the external threads 418 on the connector hub 414 along the internal threads 318 of the connector body 314. This advancement forces the leading membrane surface 420 against the piercing member 354 which pierces the leading membrane surface 420 as shown in FIG. 9d. "Still further advancement of the connector hub 414 relative to the connector body 444 314 advances the connector hub 414 against the sealing plunger stop 358 to overcome the force of the compression spring 336 and push the sealing plunger 326 out of the UV transparent section 320." Fluid can then flow back and forth from the inner lumen 330 of the transfer catheter to the inner lumen 480 of the solution set catheter. Removal of the connector hub 414 from the connector body 314 will remove the force on the sealing plunger stop 358 allowing the compression spring 356 to advance the sealing plunger 326 back into the UV transparent section 320 to seal off the UV transparent section from the inner lumen 330. As in the previously described embodiment, the position of the sealing plunger stop, the sealing plunger 326, and the sealing surface 416 are configured such that the sealing plunger 326 will seal against the inside of the UV transparent surface 320 before the sealing surface 416 is withdrawn from the UV transparent section 320 to prevent contamination of the inner lumen 330.

It will be apparent to those skilled in the art that the embodiment shown in FIGS. 9a-9d has fewer components in the solution set catheter than the previously disclosed embodiment described herein. Fewer components generally results in the advantage of a more reliable and less expensive system.

Figure 10A:
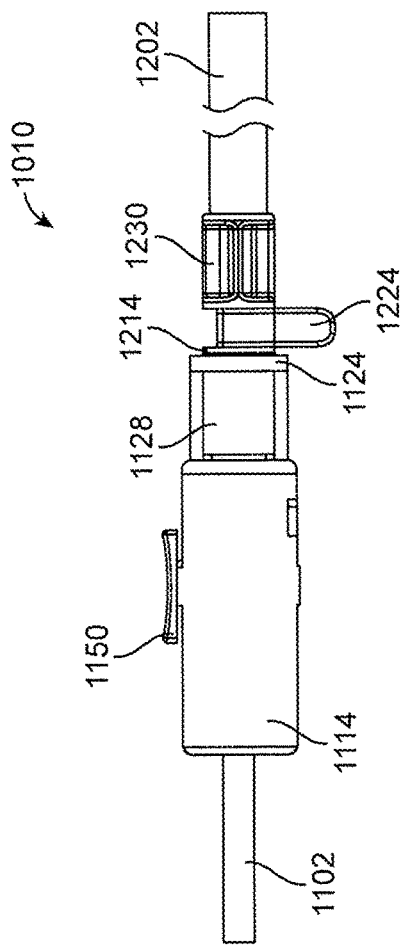
FIG. 10a is an illustration of a detailed view of still another alternate embodiment of the catheter connection system.
Figure 10B:
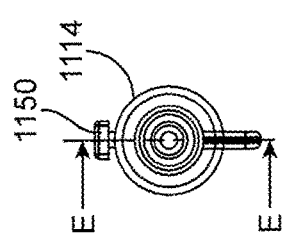
Figure 10C:
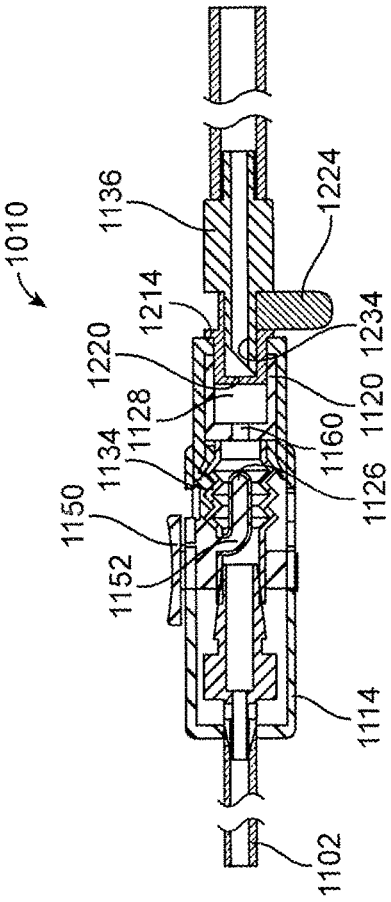
FIG. 10c is an illustration of a cross section view of an embodiment of the catheter connection system from FIG. 10b through line E-E.

Referring to FIGS. 10a-10c, an alternate embodiment of the catheter connection system 1010 is shown. The connector body 1114 of this embodiment has a seal actuator 1150 which is configured to advance a seal 1126 against an opening 1160 of a UV transparent section 1120. The seal actuator 1150 is comprised of an extended arm 1152 which connects the seal actuator 1150 to the seal 1126 through the flexible accordion membrane 1134. The flexible accordion membrane 1134 seals off around the extended arm 1152 preventing any fluid leak. The seal actuator 1152 is configured for the user to selectively seal and unseal the opening 1160 of the UV transparent section 1120. The catheter connection system 1010 also includes a connector hub 1214, a c clip 1224 and a barb hub 1230. The connector hub 1214 is configured with a leading membrane surface 1220, and the barb hub 1230 is configured with a piercing member 1234 that is position adjacent to the leading membrane surface 1220. When the seal 1126 is advanced against the opening 1160, the seal 1126 the UV transparent section 1120 and the leading membrane surface 1220 create a small controlled volume 1128 that can be disinfected with UVC light. As with previously described embodiments, after disinfection, the c clip 1224 is removed so that the barb hub 1230 can be advanced and the piercing member 1234 can penetrate the leading membrane surface 1220. The seal actuator 1150 is retracted unsealing the opening 1160 in the UV transparent section 1120 allowing fluid to flow to and from the inside of the tubular body 1102 and to and from the inside of the tubular body 1202. In this embodiment, the user is easily able to control the flow of fluid by actuating the seal actuator 1150.

Another alternate embodiment of the current invention is shown in FIGS. 11a-11c. The catheter connector system 2010 comprises a UV transparent section 2120 that has a side opening 2160. The side opening 2160 is covered with a flexible membrane 2134 which is sealed to the UV transparent section 2120 by the connector body 2114 and one or more supporting ribs 2122. In this embodiment, actuation of the seal actuator 2150 forces a ball 2152 against the flexible membrane 2134 such that the flexible membrane 2134 seals against the inside surface of the UV transparent section 2120. The flexible membrane 2134, UV transparent section 2120 and the leading membrane surface 2220 together create a small contained volume 2128 that can be disinfected with UVC light that is directed towards the small contained volume 2128 from one or more directions. After disinfection, the c clip 2224 is removed so that the barb hub 2230 can be advanced and the piercing member 2234 can penetrate the leading membrane surface 2220. The seal actuator 2150 is retracted releasing the force on the ball 2152 and allowing the flexible membrane 2134 to unseal from the inside of the UV transparent section 2120 allowing fluid to flow to and from the inside of the tubular body 2102 and to and from the inside of the tubular body 2202. In this embodiment, the user is easily able to control the flow of fluid by actuating the seal actuator 2150.

Figure 12A:
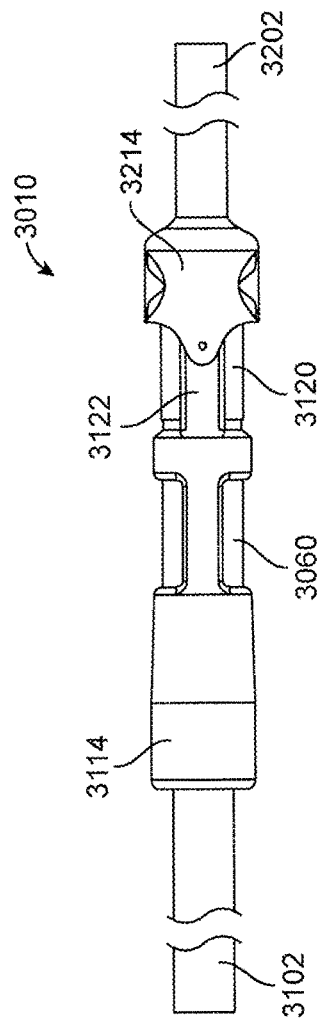
FIG. 12a is an illustration of a detailed view of another alternate embodiment of the catheter connection system.
Figure 12C:
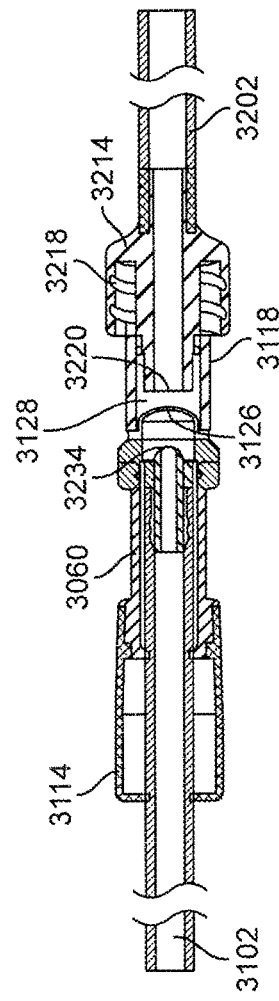
FIG. 12c is an illustration of a cross section view of an embodiment of the catheter connection system from FIG. 12b through line G-G.
Figure 12B:
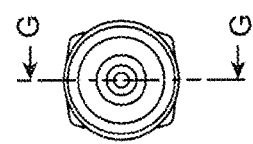

Yet another embodiment of the current invention is shown in FIGS. 12a-12c. The catheter connection system 3010 is comprised of dome seal 3126 that is position between the UV transparent section 3120 and the connector body 3114. The dome seal 3126, the UV transparent section 3120, and the leading membrane surface 3220 create a small contained volume 3128 that can be disinfected with UVC light. After disinfecting the small contained volume 3128 the connector hub 3214 is rotated advancing the leading membrane surface 3220 through a slit in the dome valve 3126 as the internal threads 3218 on the connector hub 3214 engage the external thread 3118 on the connector body 3114. After the leading membrane surface 3220 passes through the dome valve 3126 it is forced over the piercing member 3234 which penetrates the leading membrane surface 3220 allowing fluid to flow to and from the tubular body 3102 and to and from the tubular body 3202. The dome valve 3126 is configured such that the slit will close and reseal the tubular body 3102 from the UV transparent section 3120 when the connector hub 3214 is separated from the connector body 3114. The connector body 3114 is configured with a depressed section 3060 that helps the user securely grasp the connector body 3114 to advance and retract the connector hub 3214.

Figure 13A:
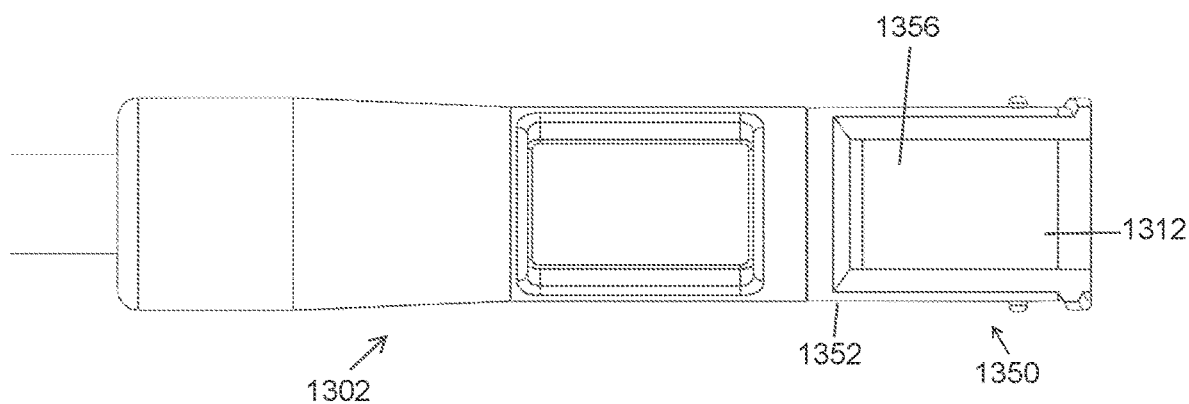
FIGS. 13A and B illustrate an embodiment of a transfer catheter.
Figure 13B:
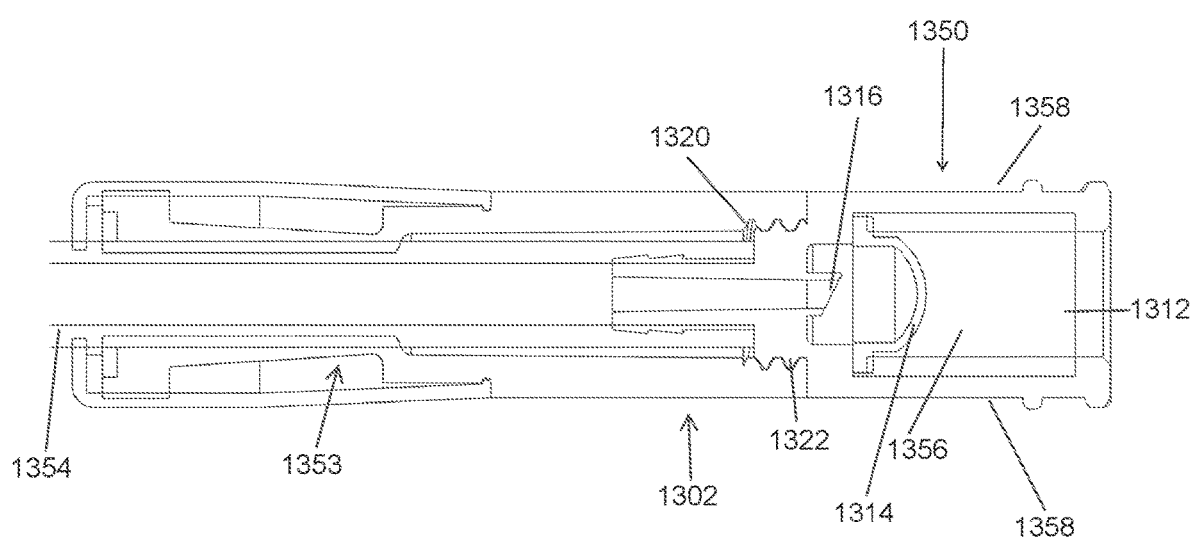
FIG. 13C illustrates and embodiment of a solution set catheter.
Figure 13C:
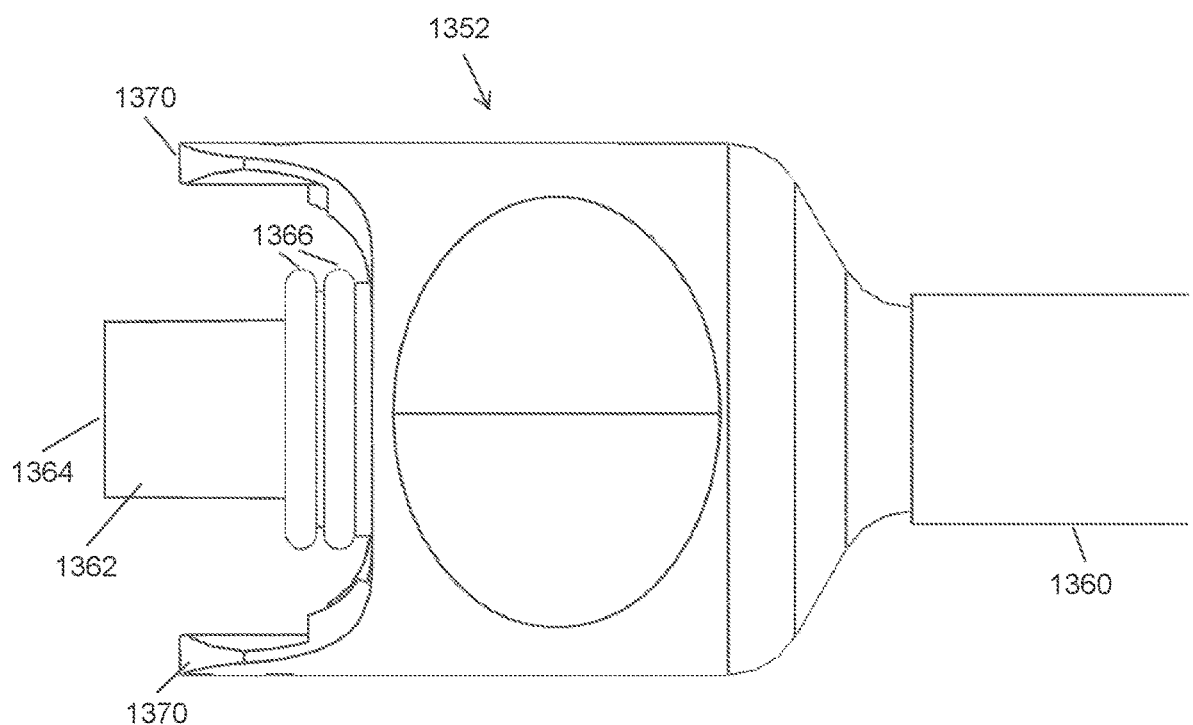

FIGS. 13A-13C show another embodiment of transfer and solution set catheters similar to those shown in FIGS. 12A-12C. FIG. 13A illustrates a side view of a transfer catheter 1302 comprising connector piece 1350. A sectioned view is shown in FIG. 13B. The transfer catheter connector 1350 connects to the catheter tubing 1354 (e.g., using a barb fitting or solvent bonding). A clamp 1353 (e.g., a pinch clamp) is positioned proximal to the connector piece 1350. The clamp 1353 can help prevent leakage and contamination between dialysis sessions. The transfer catheter connector 1350 comprises a UV-transparent window portion 1312 positioned at its distal end. The window 1312 includes a round tube 1356 supported by two ribs 1358 of the connector body. The ribs 1358 can comprise beveled edges 1359 which can allow better exposure of the UV-window 1312 to applied UV light. Fewer or more panes are also possible. The window can comprise quartz, in some embodiments. Other materials or combinations or materials are also possible (e.g., topas).

Proximal to the window 1312 is a valve 1314. The valve 1314 can comprise a dome valve, as shown in FIG. 13B. A piercing member 1316, such as a barb (or needle, spike, point, etc.) is positioned proximal to or within the valve 1314. The valve 1314 provides a seal and allows for passage of the piercing member 1316 upon proximal deflection of the dome portion, but is configured to seal upon subsequent distal deflection of the valve dome. Valves other than dome valves (e.g., flat valves, and X-slot valves) are also contemplated.

Threads 1320 on the transfer catheter 1302 are shown connected to threads 1322 on the connector 1350. Other modes of connection are also possible. For example, the disinfection portion 1318 can be joined to the transfer catheter 1302 using an ultrasonic welding step, a solvent bonding procedure, a snap fit, an adhesive, or the like. In some embodiments, the connector 1350 is formed integrally with the transfer catheter.

FIG. 13C illustrates a side view of an embodiment of a solution set connector 1352. The connector can connect to the tubing 1360 (e.g., using a barb fitting or solvent bonding). The tubing 1360 can fluidly connect to a lumen 1362 of the solution set connector 1352 that extends proximally beyond the rest of the solution set connector 1352. In some embodiments, the tubing 1360 can itself run through the connector 1352 to the proximal end. The lumen 1362 comprises a film barrier 1364 at its proximal end. The barrier film 1364 provides a seal between the outside environment and the solution set tubing. The film 1364 can be pierced by the piercing member 1316 by complete connection of the transfer catheter 1302 and solution set catheter 1304. The barrier film 1364 can comprise an elastomeric material, a metallic film, a polymer film, or a combination of these.

The lumen 1362 comprises one or more seals 1366 (e.g., O-rings) positioned around the lumen 1362. The seals 1366 are configured to sealingly interfere with an inner surface of the UV-transparent window 1312 as the lumen 1362 is inserted within the window 1312. The seals 1366 can define a boundary for and seal the fluid path, as described in more detail below. The connector comprises an outer connection region 1370 configured to surround the transfer catheter connector 1350 as the transfer catheter connector is inserted into the solution set catheter (FIG. 14).

Figure 14:
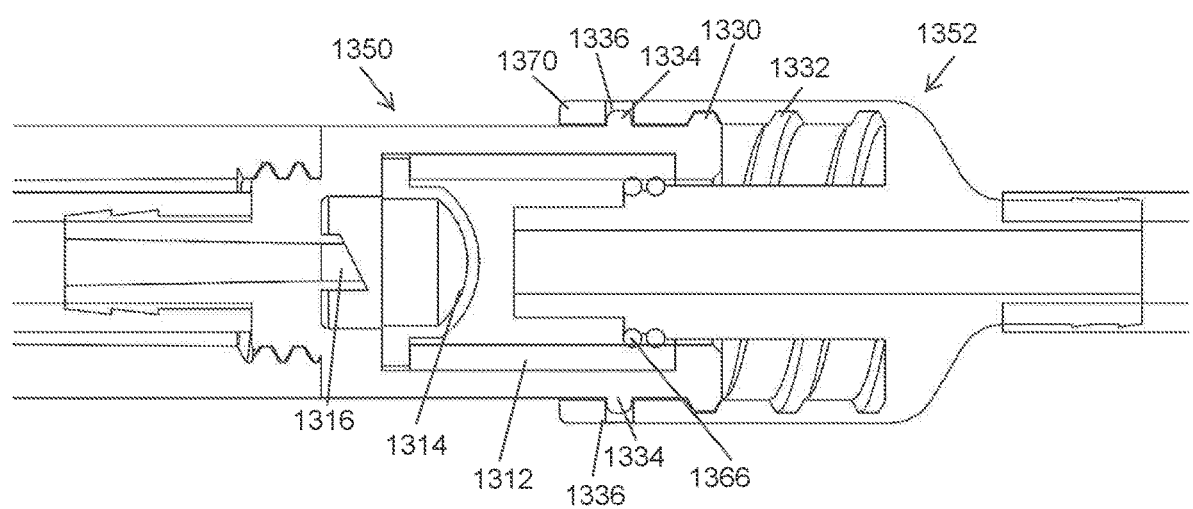
FIG. 14 is an illustration of an embodiment of a transfer catheter connector connected to a solution set connector in a disinfection position.

The transfer catheter connector 1350 is shown connected with the solution set catheter connector 1352 in FIG. 14 via a threaded connection. In some embodiments, a user turns the connectors 1350, 1352 (e.g., about ¼ turn) to move the catheters into the position shown in FIG. 14. Other configurations for connecting the catheters are also contemplated. For example, in some embodiments, a linear motion where the user presses the connectors together is contemplated. A distal end of the transfer catheter connector 1350 is inserted within the outer connection region 1370 of the solution set catheter connector 1354. Threads 1330 on the transfer catheter 1302 are threaded to threads 1332 on the solution set catheter 1304. The transfer catheter connector 1350 includes stops 1334 configured to interact with feature 1336 on an inner surface of the solution set connector. The stop 1334 can include a protrusion or bump configured to interfere with a feature 1336 comprising a depression or opening on the solution set connector. FIG. 14 illustrates the catheters 1302, 1304 connected in a disinfection position, as will be described in more detail below.

Figure 15:
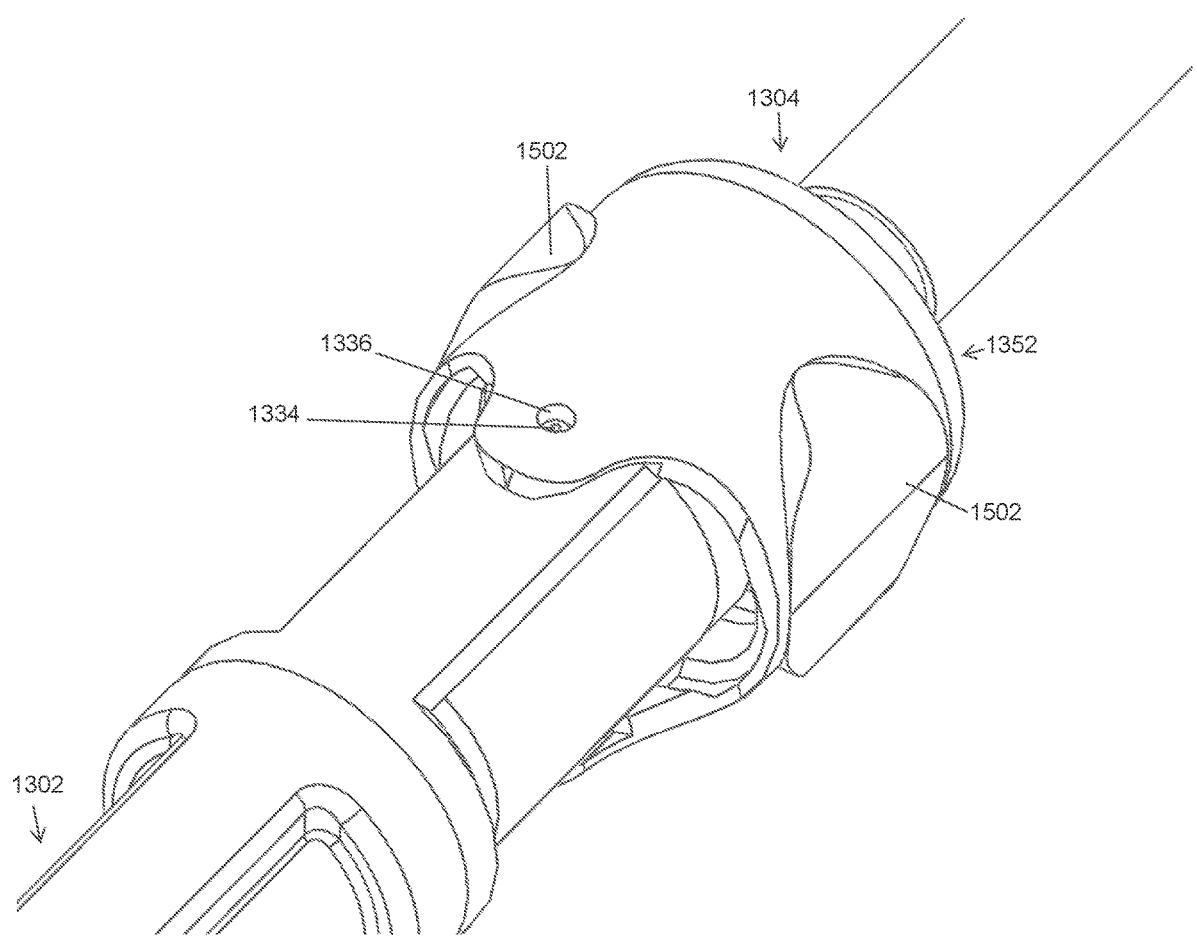
FIG. 15 illustrates a stop feature of the connectors of FIG. 14.

FIG. 15 better illustrates the stop 1334 of the transfer catheter connector 1350 and mating feature 1336 of the solution set connector 1352. The stop 1334 and mating feature 1336 provide audio and/or tactile feedback to a user, providing a positive stop when the catheters are in the proper position for disinfection. This feature provides a safety to prevent over-insertion and puncture of solution set seal prior to disinfection. After completion of disinfection, the stop forces a user to actively disengage the stop to advance the solution set tubing towards the barb to allow for initiation of the drain phase. For example, in some embodiments, the user must squeeze the solution set connector using finger grips 1502 to disengage the stop 1334 before advancing the solution set connector. The finger grips 1502 can advantageously indicate where a user should press to allow disengagement of the stop 1334. The finger grips 1502 can also advantageously allow for easier disengagement by providing a comfortable and easy spot to squeeze the connector 1352. The stops 1334 and mating features 1336 can also help to ensure that the catheters are not inadvertently disconnected. For example, when a user is moving the catheters out of the flow position (e.g., at the end of a dialysis session), the stops can help ensure that the catheters are not disconnected prematurely. FIG. 15 shows the catheters 1302, 1304 in the disinfection position as indicated by the engagement of the stop 1334 of the transfer catheter connector 1350 with the mating features 1336 of the solution set connector 1352.

Figure 16:
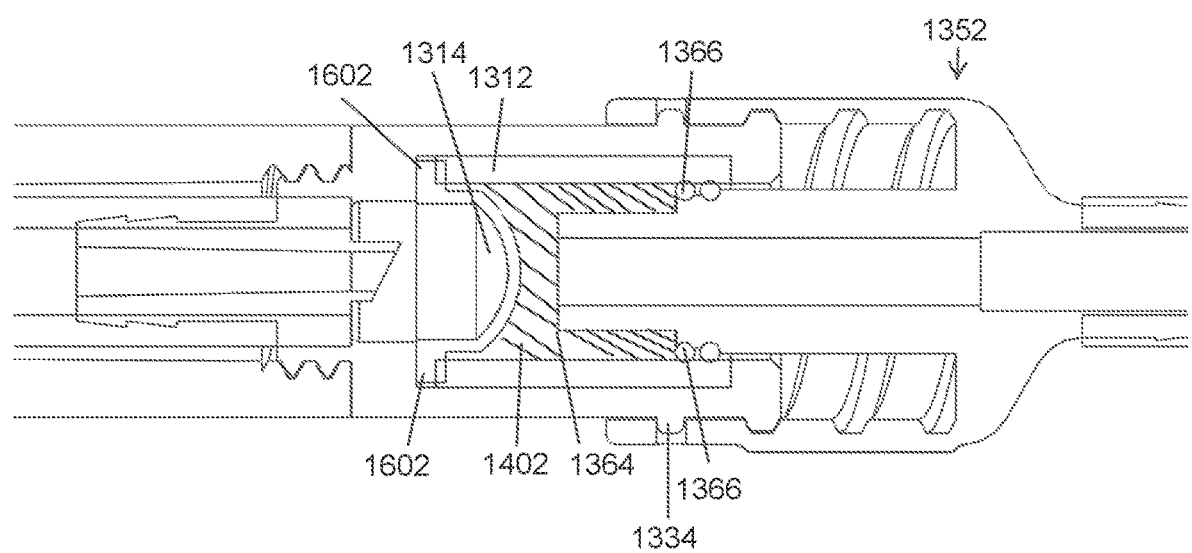
FIG. 16 illustrates an embodiment of the kill zone of FIG. 14.

FIG. 16 illustrates the same view as FIG. 14, but also shows various regions of possible contamination within the connected catheter system. The kill zone 1402 is shown as the space within the UV-transparent region 1312 bounded by the valve 1314 on the transfer catheter side. A flange 1602 extending around the dome valve 1314 can interfere sealingly with an edge of the UV-transparent window 1312. The kill zone 1402 is bounded on the solution set side by the distal end of the solution set catheter including barrier film and the seals 1366 on the solution set catheter side. The seals 1366 and the valve 1314 help to minimize the volume to be disinfected by minimizing the volume of the fluid path of dialysate fluids. The seals 1366 being provided on the lumen of the solution set catheter allows the disinfected zone to be maintained after disinfection and during the transition from the disinfection to the flow position as the seals 1366 move towards the transfer catheter 1302 to shorten the fluid path. For example, if the seal were on an inner surface of the transfer catheter connector 1350, transition from the disinfection to the flow zone would move an untreated portion of the solution set connector 1352 past the seal and into the fluid path.

The kill zone 1402 includes the region of potential contamination within fluid path as well as the region capable of irradiation with UV light. As shown in FIG. 16, the kill zone 1402 extends past the seals 1366 on the solution set side of the catheter connection. This portion of the solution set connector 1352 is not required to be disinfected as the seals 1366 prevent any contamination contained therein from entering the fluid path area. However, the disinfection of this additional area provides an extra level of safety that can help to provide confidence in complete disinfection of the fluid path region. In some embodiments, the volume of the kill zone is about 0.25-0.55 cc, for example about 0.4 cc.

Figure 17:
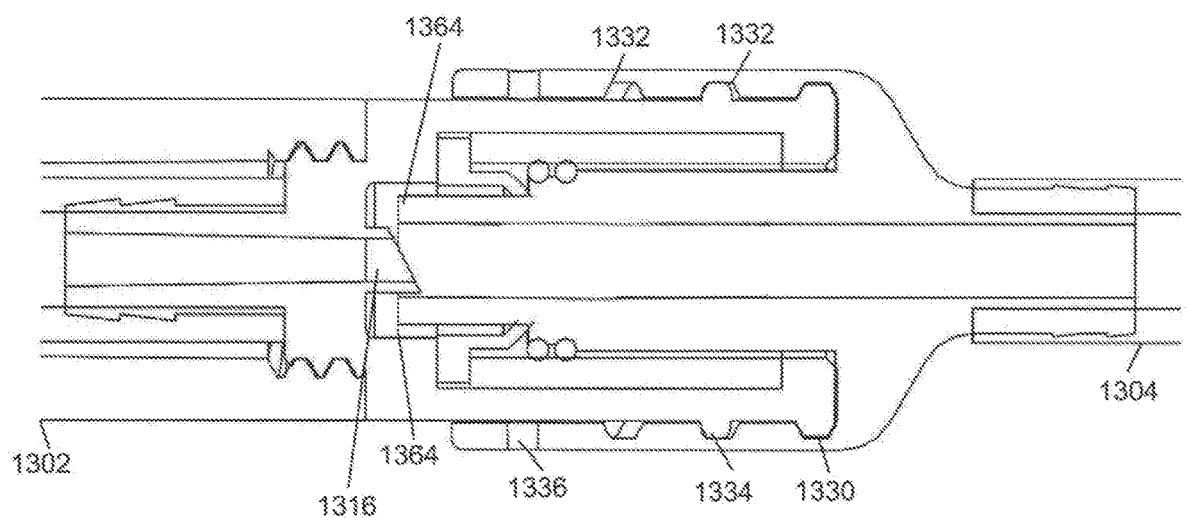
FIG. 17 illustrates the connectors of FIG. 14 positioned in a flow position.

FIG. 17 illustrates the transfer catheter 1302 and the solution set catheter 1304 in the flow position, in which the piercing member 1316 has ruptured the film barrier 1364, creating a fluid path between the transfer catheter 1302 and the solution set catheter 1304. The transfer catheter 1302 and solution set catheter 1304 transition from the disinfection position to the flow position by disengaging stop 1334 from mating features 1336 and further inserting the transfer catheter connector 1350 into the solution set connector 1352. In this embodiment, the further insertion comprises rotating the connectors 1350, 1352 relative to one another to advance the solution set connector 1352 towards the transfer catheter connector via threads 1330, 1332.

In some embodiments, advancing the catheters 1302, 1304 from the flow position to the disinfection position comprises rotating the solution set connector 1352 about one full turn. Thread thickness and pitch can be selected to enable one full turn to transition the system from disinfection to flow position. Turning the catheters one full turn to transition to the flow position can provide ease of use of the system as an average user should be able to complete one full turn in on motion.

Figure 18:
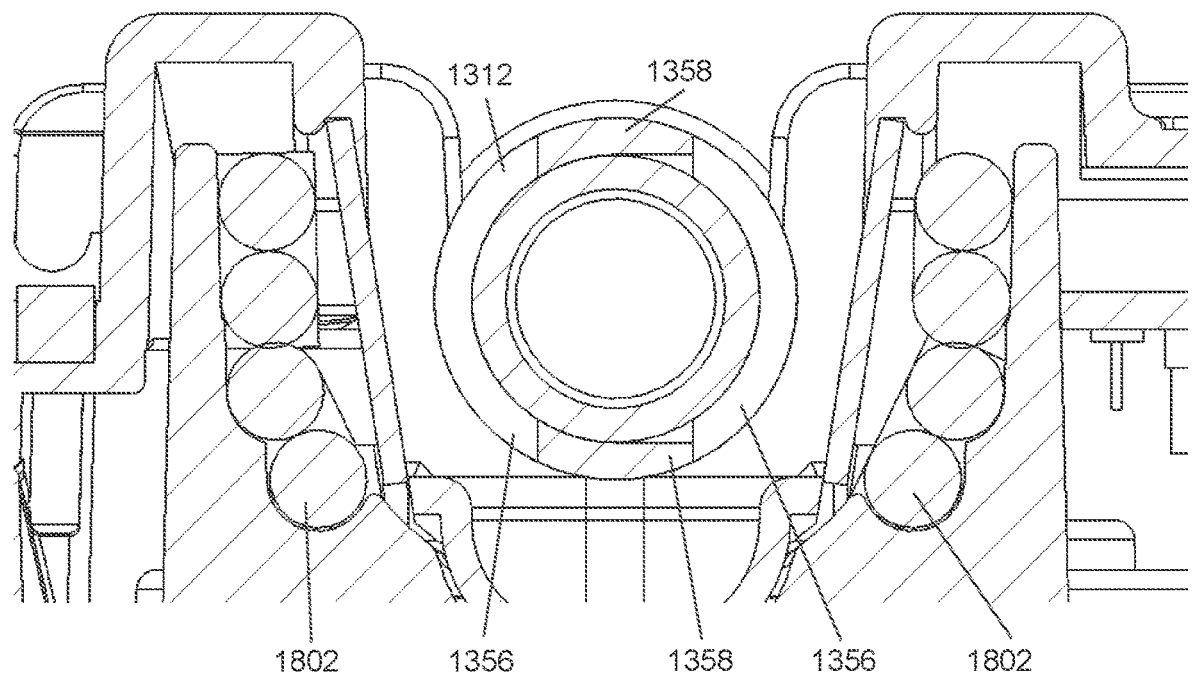
FIG. 18 illustrates the connectors of FIG. 14 positioned within a UV disinfection unit.

To disinfect the catheters when in the disinfection system, the catheter connection can be exposed to UV radiation. For example, the catheter connection can be placed in a UV disinfection unit such as the unit described in U.S. Provisional Application No. 62/052,164 ("the '164 Application"), filed Sep. 18, 2014, the disclosure of which is herein incorporated by reference in its entirety. A disinfection unit can be configured to ensure that the connectors are properly positioned within the unit to allow for optimal UV exposure and disinfection. FIG. 18 illustrates a cross-sectional view of the connectors 1350, 1352 positioned within the disinfection unit of the '164 Application. The UV lamps 1802 are positioned on either side of the catheters 1302, 1304. The catheter connection is positioned such that the unobstructed portion of UV transparent tube 1356 are generally facing the UV lamps while ribs 1358 are positioned at the top and bottom of the unit, in the positions least exposed to UV irradiation. The convex shape of the dome valve 1314 (not shown in FIG. 18) can allow for thorough disinfection, as the entire surface area of the valve is in a position to be directly exposed to UV light.

An example method of using the disinfection system described herein during a dialysis session follows. The user first assembles required equipment and supplies (e.g., stand for dialysate bag). The user inspects the dialysate bag set, opens the outer packaging of the bag set and removes the dust cover. The previous solution set catheter can be removed from the transfer catheter. A new solution set catheter is attached to the transfer catheter and moved into the disinfection position (e.g., by turning the catheters relative to one another ¼ of a turn). The catheter connectors 1350, 1352 are exposed to a UV light source (e.g., by placing the connectors in a unit such as that shown in FIG. 18). The UV light source is activated to expose the connectors 1350, 1352. The connectors can then be removed from the disinfection unit, if one was used. The connectors are then transitioned to the flow position (e.g., by turning the catheters relative to one another 1 full turn. The tube clamp on the transfer catheter is opened. The user performs dialysate drain, flush, and fill, per the bag manufacturer's instructions. The transfer catheter clamp is closed. The solution set catheter is retracted to the initial position (disinfection position). The solution set catheter can be clamped off and the bag set removed from the solution set catheter. Alternatively, the solution set catheter can be removed and an optional cap can be positioned on the transfer catheter. In some embodiments, this cap can be irradiated with UV light as a last step in the procedure.

It will be appreciated that while the disinfection system has been described in connection with peritoneal dialysis, the transfer catheter and/or solution set connectors can be used in numerous other applications, medical or otherwise. For example, features of the connectors/valves disclosed in PCT Application No. PCT/US 15/25352, filed Apr. 10, 2015, and entitled "Connector Disinfection System" and U.S. application Ser. No. 14/731,110, filed Jun. 4, 2015, and entitled "Transfer Catheter for Ultraviolet Disinfection" the disclosures of which are incorporated by reference herein in their entireties, can be used in the connector systems described herein.

Although the embodiments described herein contain particular combinations of the various elements of the current invention, it will be obvious to those skilled in the art that these elements can be combined in many other variations to provide the features needed without departing from the current invention. In the description herein UVC light was mention as a method of disinfection of microorganisms. Although the UVC wave length of approximately 260 nanometer wavelength is particularly effective in disinfection of microorganisms, longer UVB wavelengths can be used for disinfection without departing from the current invention. The elements of the current invention are depicted as generally cylindrical in shape as is typical of most catheter systems. However, any element, portion of the system, or the entire system can be in a non-cylindrical shape to achieve the desired function without departing from the current invention.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An ultraviolet (UV) catheter connection disinfection system, comprising:
   a first connector comprising a UV transparent region at a first end of the first connector, a sealing plunger biased into a position inside the UV transparent region and proximal to the first end of the first connector, and a piercing member; and
   a second connector comprising a leading membrane surface mounted on a connector hub, and a sealing surface for sealing against the UV transparent region at a first end of the second connector, wherein the piercing member is configured to pierce the leading membrane surface;
   wherein the first end of the second connector is configured to mate with the first end of the first connector in a first disinfection position in which the leading membrane surface is intact and the sealing plunger is configured to create a seal between the sealing plunger and an inside portion of the UV transparent region, blocking flow through the first connector, and in a second flow position in which the leading membrane surface is punctured by the piercing member and the sealing plunger is deflected into the second flow position by advancement of the connector hub toward the piercing member, and wherein, in the first disinfection position, a sealed disinfection zone is defined by the sealing plunger, the UV transparent region, the leading membrane surface and the sealing surface and
   wherein the sealing plunger is biased into said position inside the UV transparent region such that withdrawal of the connector hub away from the piercing member moves the sealing plunger to thereby restore the seal between the sealing plunger and the inside portion of the of UV transparent region.

2. The system of claim 1, wherein the sealing surface comprises at least one of an o-ring, a wiper shaped blade, and a spring energized seal.

3. The system of claim 1, wherein the sealing surface comprises at least one of silicone, butyl rubber, PTFE, and neoprene.

4. The system of claim 1, wherein the leading membrane surface comprises at least one of metallic foil and plastic foil.

5. The system of claim 1, wherein the UV transparent region comprises at least one of quartz glass, cyclic olefin copolymer, and TPX (polymethylpentene polyolefins).

6. The system of claim 1, further comprising a spring to effect said bias of the sealing plunger.

7. The system of claim 1, wherein a second end of the second connector is configured to removably connect to a tubular member, the tubular member removable from the second connector.

8. The system of claim 1, wherein the first connector is configured to connect to an indwelling catheter.

9. The system of claim 1, wherein the second connector is configured to connect to a solution set catheter.

10. The system of claim 1, wherein the first connector and the second connector comprise threads to hold the first and second connectors together.

11. The system of claim 1, wherein the first connector comprises a spring configured to advance the sealing plunger against an opening of the UV transparent region.

12. The system of claim 1, wherein the sealing plunger and the leading membrane surface are resealable.

13. The system of claim 1, wherein the sealing plunger and the leading membrane surface are single use components.

14. The system of claim 1, wherein the sealing plunger is resealable and the leading membrane surface is a single use component.

15. The system of claim 1, wherein the sealing plunger is a single use component and the leading membrane surface is resealable.

* * * * *